United States Patent [19]
Hutchinson

[11] Patent Number: 5,910,504
[45] Date of Patent: Jun. 8, 1999

[54] HETERO-AROMATIC RING SUBSTITUTED PHENYLOXAZOLIDINONE ANTIMICROBIALS

[75] Inventor: Douglas K. Hutchinson, Kalamazoo, Mich.

[73] Assignee: Pharmacia & Upjohn, Kalamazoo, Mich.

[21] Appl. No.: 08/875,800

[22] PCT Filed: Jan. 29, 1996

[86] PCT No.: PCT/US96/00718

§ 371 Date: Aug. 4, 1997

§ 102(e) Date: Aug. 4, 1997

[87] PCT Pub. No.: WO96/23788

PCT Pub. Date: Aug. 8, 1996

Related U.S. Application Data

[63] Continuation-in-part of application No. 08/384,278, Feb. 3, 1995, abandoned.

[51] Int. Cl.[6] .......................... C07D 413/10; A61K 31/42
[52] U.S. Cl. .......................... 514/376; 548/231; 548/255; 548/263.2; 548/335.5; 548/338.1; 548/374.1; 548/375.1; 548/469; 548/561; 546/113; 546/117
[58] Field of Search .............. 548/231; 514/376

[56] References Cited

U.S. PATENT DOCUMENTS

| | | | |
|---|---|---|---|
| 4,801,600 | 1/1989 | Wang et al. | 514/376 |
| 4,921,869 | 5/1990 | Wang et al. | 514/376 |
| 4,948,801 | 8/1990 | Carlson et al. | 548/231 |
| 5,254,577 | 10/1993 | Carlson et al. | 548/231 |
| 5,561,148 | 10/1996 | Gante et al. | 548/232 |
| 5,654,428 | 8/1997 | Barbachyn et al. | 544/238 |
| 5,668,286 | 9/1997 | Yamada et al. | 546/209 |
| 5,684,023 | 11/1997 | Riedl et al. | 548/231 |
| 5,698,574 | 12/1997 | Riedl et al. | 514/376 |

FOREIGN PATENT DOCUMENTS

| | | |
|---|---|---|
| 312000 | 4/1989 | European Pat. Off. . |
| 316594 | 5/1989 | European Pat. Off. . |
| 0352781 | 1/1990 | European Pat. Off. . |
| 352781 | 1/1990 | European Pat. Off. . |
| WO90/02744 | 3/1990 | WIPO . |
| 93 09103 | 5/1993 | WIPO . |
| WO93/23384 | 11/1993 | WIPO . |
| 95-07271 | 3/1995 | WIPO . |
| 93-09103 | 5/1995 | WIPO . |
| 96-23788 | 8/1996 | WIPO . |
| 97-31917 | 9/1997 | WIPO . |

OTHER PUBLICATIONS

Gregory W. A., et al., *J. Med. Chem.*, 32, 1673–81 (1989).
Gregory W. A., et al., *J. Med. Chem.*, 33, 2569–78 (1990).
Wang C., et al., *Tetrahedron*, 45, 1323–26 (1989).
Brittelli, et al., *J. Med. Chem.*, 35, 1156 (1992).

*Primary Examiner*—Donald G. Daus
*Attorney, Agent, or Firm*—Donald L. Corneglio; Lucy X. Yang

[57] ABSTRACT

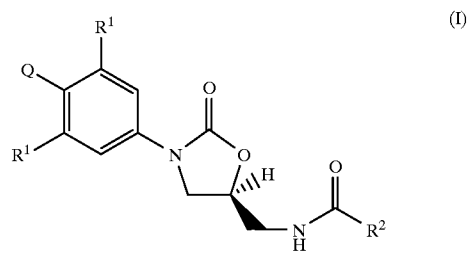

A hetero-aromatic (Q) substituted phenyloxazolidinone antimicrobial of Formula (I) wherein Q is a 5-member hetero-aromatic having from one to four nitrogen atoms or alternatively a benzoannulated 5-member hetero-aromatic having from one to four nitrogen atoms where $R^1$ is independently H, $OCH_3$, F, or Cl; $R^2$ is hydrogen, $C_1$–$C_8$ alkyl (optionally substituted with one or more of F, Cl, hydroxy, $C_1$–$C_8$ alkoxy, $C_1$–$C_8$ acyloxy), $C_3$–$C_6$ cycloalkyl, amino, $C_1$–$C_8$ alkylamino, $C_1$–$C_8$ dialkylamino, $C_1$–$C_8$ alkoxy; and each Q is optionally substituted with one or more of H, F, Cl, Br, $OR^4$, $SR^4$, $S(O)_nR^4$ (n=1 or 2), CN, $O_2CR^4$, $NHCOR^4$, $NHCO_2R^4$, $NHSO_2R^4$, $CO_2R^4$, $CON(R^4)_2$, $COR^4$, $C_1$–$C_8$ straight or branched chain alkyl or $C_3$–$C_8$ cycloalkyl, optionally substituted with one or more of (a)–(m), or Phenyl, optionally substituted with one or more of the preceeding groups listed under (a)–(n); and $R^4$ is H, $C_1$–$C_6$ straight or branched chain alkyl or $C_3$–$C_8$ cycloalkyl optionally substituted with one or more of fluorine, chlorine, hydroxy, $C_1$–$C_4$ alkoxy, $C_1$–$C_4$ acyl, $C_1$–$C_4$ acyloxy, or $O_2CCH_2N(CH_3)_2$, or Phenyl, optionally substituted with one or more of fluorine, chlorine, $C_1$–$C_4$ straight or branched chain alkyl, hydroxy, $C_1$–$C_4$ alkoxy, $C_1$–$C_4$ acyl, $C_1$–$C_4$ acyloxy, or $O_2CCH_2N(CH_3)_2$.

19 Claims, No Drawings

HETERO-AROMATIC RING SUBSTITUTED PHENYLOXAZOLIDINONE ANTIMICROBIALS

CROSS-REFERENCE TO RELATED APPLICATION

This application is the 371 (National Phase) patent application of PCT application PCT/US96/00718, filed Jan. 29, 1996, which was a continuation-in-part application of U.S. patent application Ser. No. 08/384,278, filed Feb. 3, 1995, now abandoned.

BACKGROUND OF THE INVENTION

The subject invention discloses new and useful phenyloxazolidinone compounds having a nitrogen containing hetero-aromatic ring substitution attached through one of the nitrogen atoms. More particularly a 5-member nitrogen containing aromatic ring having from 1 to 4 nitrogen atoms one of which binds to the phenyloxazolidinone. The compounds are useful antimicrobial agents, effective against a number of human and veterinary pathogens, including gram-positive aerobic bacteria such as multiply-resistant staphylococci, streptococci and enterococci as well as anaerobic organisms such as Bacteroides spp. and Clostridia spp. species, and acid-fast organisms such as *Mycobacterium tuberculosis, Mycobacterium avium* and Mycobacterium spp.

INFORMATION DISCLOSURE

The present compounds are related by their phenyloxazolidinone ring structure to the compounds disclosed in the publications below except that the subject compounds have a nitrogen containing hetero-aromatic ring substitution attached to the phenyloxazolidinone by one of the nitrogen atoms. This attachment point facilitates a different but easier synthesis than a corresponding carbon—carbon bond structure and therefore presents an advantage over such compounds. The instant compounds are unique and have useful antibacterial activity.

WO93/23384 application discloses oxazolidinones containing a substituted diazine moiety and their uses as antimicrobials.

WO93/09103 application discloses substituted aryl and heteroaryl-phenyl-oxazolidinones useful as antibacterial agents. In one aspect, it discloses 5-member nitrogen hetero-aromatic rings attached to a phenyloxazolidinone although there is no synthesis disclosed which would permit attachment through the nitrogen atom (see, Chart C (y, w, ee and ff)).

WO90/02744 application discloses 5'indolinyl-5β-amidomethyloxazolidinones, 3-(fused-ring substituted) phenyl-5β-amidomethyloxazolidinones, and 3-(nitrogen substituted)phenyl-5β-amidomethyloxazolidinones which are useful as antibacterial agents.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

U.S. Pat. No. 5,254,577 discloses nitrogen hetero-aromatic rings attached to phenyloxazolidinone but not by the hetero-aromatic nitrogen (see, Col. 19 and 43).

SUMMARY OF THE INVENTION

In one aspect the subject invention is a compound of structural Formula I:

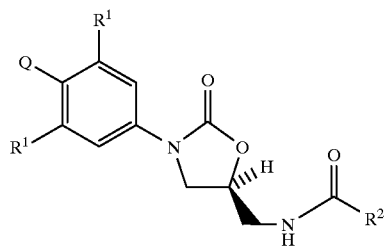

or pharmaceutically acceptable salts thereof wherein:

Q is a hetero-aromatic 5-member ring bound to the aromatic ring of I at the nitrogen of the structures i, ii, iii, iv, v, vi, vii, viii, or ix:

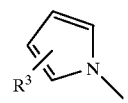

i

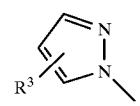

ii

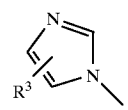

iii

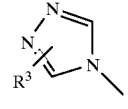

iv

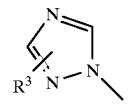

v

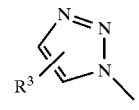

vi

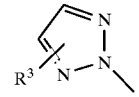

vii

3

-continued

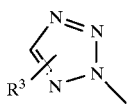 viii

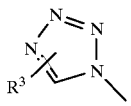 ix or alternatively Q can be a benzoannulated heteroaromatic 5-member ring bound to the aromatic ring of I at the nitrogen of the structures x, xi, xii, xiii, xiv, xv, xvi or xviii:

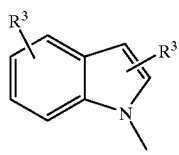 x

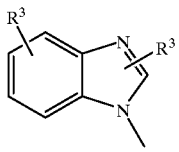 xi

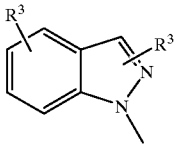 xii

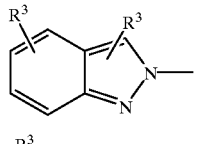 xiii

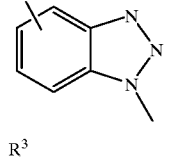 xiv

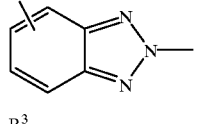 xv

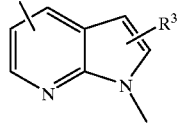 xvi

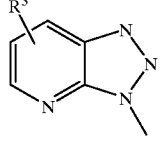 xvii

4

-continued

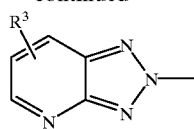 xviii $R^1$ is independently H, $OCH_3$, F, or Cl;

$R^2$ is
  (a) hydrogen,
  (b) $C_1$–$C_8$ alkyl optionally substituted with one or more of the following: F, Cl, hydroxy, $C_1$–$C_8$ alkoxy, $C_1$–$C_8$ acyloxy;
  (c) $C_3$–$C_6$ cycloalkyl;
  (d) amino;
  (e) $C_1$–$C_8$ alkylamino;
  (f) $C_1$–$C_8$ dialkylamino;
  (g) $C_1$–$C_8$ alkoxy;

$R^3$ is each independently selected from
  (a) H,
  (b) F, Cl, Br,
  (c) $OR^4$,
  (d) $SR^4$,
  (e) $S(O)_n R^4$ (n is 1 or 2),
  (f) CN,
  (g) $O_2 CR^4$,
  (h) $NHCOR^4$,
  (i) $NHCO_2 R^4$,
  (j) $NHSO_2 R^4$,
  (k) $CO_2 R^4$,
  (l) $CON(R^4)_2$,
  (m) $COR^4$,
  (n) $C_1$–$C_8$ straight or branched chain alkyl or $C_3$–$C_8$ cycloalkyl, optionally substituted with one or more of (a)–(m), or
  (o) Phenyl, optionally substituted with one or more of the preceeding groups listed under (a)–(n); and $R^4$ is
  (a) H,
  (b) $C_1$–$C_6$ straight or branched chain alkyl or $C_3$–$C_8$ cycloalkyl, optionally substituted with one or more of fluorine, chlorine, hydroxy, $C_1$–$C_4$ alkoxy, $C_1$–$C_4$ acyl, $C_1$–$C_4$ acyloxy, or $O_2 CCH_2 N(CH_3)_2$, or
  (c) Phenyl, optionally substituted with one or more of fluorine, chlorine, $C_1$–$C_4$ straight or branched chain alkyl, hydroxy, $C_1$–$C_4$ alkoxy, $C_1$–$C_4$ acyl, $C_1$–$C_4$ acyloxy, or $O_2 CCH_2 N(CH_3)_2$.

DETAILED DESCRIPTION OF THE INVENTION

The present invention discloses novel substituted 5-member nitrogen heterocyclic phenyloxazolidinones according to structural Formula I above.

"Alkyl" means carbon atom chains having the designated number of carbon atoms which can be either straight chained or branched.

"Alkoxy" means the designated number of carbon atoms attached to an oxygen forming such groups as methoxy (—$OCH_3$), ethyloxy, butyloxy, etc. and isomeric forms thereof.

"Acyloxy" means the designated number of carbon atoms to form an organic acid where the OH group has been deleted, such as acetyl, $CH_3 CO$—; benzoyl, $C_6 H_5 CO$—.

"Cycloalkyl" means the designated number of carbon atoms forming cyclopropyl, cyclobutyl, cyclopentyl, cyclohexyl, etc. and isomeric forms thereof.

"Amino" means an $NH_2$, "alkylamino" is where one of the hydrogen positions is replaced by an alkyl and "dialkylamino" is where both hydrogens are replaced by an alkyl group.

"Pharmaceutically acceptable salts" are acid addition salts which can be prepared by any of the art recognized means. Typical, acid addition salts include hydrochloride, hydrobromide, hydroiodide, sulfate, phosphate, acetate, propionate, lactate, malate, succinate, tartrate, cyclohexanesulfamates, methanesulfonates, ethanesulfonates, benxenesulfonates, toluenesulfonates, fumarates and other pharmaceutically acceptable couter ions for amines.

The compounds are useful as antimicrobial agents, effective against a number of human and veterinary pathogens, particularly aerobic Gram-positive bacteria, including multiply-antibiotic resistant staphylococci and streptococci, as well as anaerobic organisms such as bacteroides and clostridia species, and acid-fast organisms such as *Mycobacterium tuberculosis* and other mycobacterium species.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, patients suffering from an antimicrobial infection, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention are advantageously administered orally in solid and liquid dosage forms.

The most preferred compounds in this series would be prepared as the optically pure enantiomers having the (S)-configuration according to the Cahn-Ingold-Prelog notation at C5 of the oxazolidinone ring. Optically pure material could be prepared by one of a number of asymmetric syntheses or by resolution from a racemic modification by selective crystallization of a salt from, for example, the racemic modification of intermediate amine 10 (as described in Chart II) with an appropriate optically active acid such as dibenzoyl tartarate or 10-camphorsulfonic acid, followed by treatment with base to afford the optically active amine. Although the (S)- enantiomer of this series of compounds is preferred since it is pharmacologically active as an antibacterial agent, the racemic modification is also useful in the same manner as the pure (S)- enantiomer: the difference being that twice as much racemic material is required to elicit the same antibacterial effect. In addition, it will be apparent to those skilled in the art that when a chiral center exists in any of the substituents bonded to Q that diastereomers are possible. These diastereomers, either in the racemic or configurationally enriched forms, are within the scope of compounds of structural Formula I of this invention.

The preferred method of preparation of compounds of structural Formula I in highly enantiomerically enriched form is depicted in Charts I—VIII.

As shown in Chart I, 5-ring heterocyclics of general structure 1 (where n=number of nitrogen atoms in the ring), available either commercially or by syntheses described in the literature (see for example, Katritzky, et al. in "Comprehensive Heterocyclic Chemistry") are treated with a substituted nitrobenzene derivative 2 (Y is halogen or trifluoromethanesulfonyloxy) in a suitable base and solvent combination, for example potassium carbonate in DMSO, at a suitable temperature, typically ambient to 90° C., to afford adduct 3. This method works well for 5-ring heterocyclics such as imidazole, pyrazole, and the like. For 5-ring heterocyclics 1, such as pyrrole or indole and the like, the heterocyclic is added to a suspension of a strong base such as sodium hydride, potassium tert-butoxide, or the like in THF or DME or similar solvents to form the alkalai metal salt 4, which is then treated with nitroaromatic 2 at temperatures in the range of 0° C. to the reflux temperature of the solvent to afford adduct 3. The nitro derivative 3 is then reduced by catalytic hydrogenation in the presence of a suitable catalyst, such as palladium on carbon, W-2 Raney nickel or platinum on sulfide carbon, in a suitable solvent, such as ethyl acetate, THF, methanol or combinations therof, to afford the aniline derivative 5. When THF is used as solvent for this reduction, it is not necessary to remove the catalyst by filtration or to isolate aniline derivative 5, but merely to purge the reaction vessel with an inert gas such as nitrogen and add saturated sodium bicarbonate solution and treat the resulting cooled reaction mixture with either benzyl or methyl chloroformate to give the corresponding benzyl (R is $CH_2Ph$) or methyl carbamate (R is $CH_3$) derivatives 6.

Either of the carbamate derivatives 6 can be deprotonated with a lithium base such as n-butyllithium, lithium diisopropylamide (LDA), or lithium bis(trimethylsilyl)amide (LHMDS) in a suitable solvent such as THF, N,N-dimethylformamide (DMF), or mixtures thereof, at a suitable temperature, typically −78° C. to −40° C. to give a lithiated intermediate which is directly treated with (R)-(−)-glycidyl butyrate. Warming this reaction mixture to ambient or higher temperatures then affords the (hydroxymethyl) oxazolidinone 7 in highly enantiomerically enriched form.

Chart II describes the conversion of (hydroxymethyl) oxazoldinone 7 into oxazoldinone antibacterial agents of Structural Formula I. As shown, compound 7 can be converted into the corresponding mesylate (R=$CH_3$) or tosylate (R=p-$CH_3C_6H_4$) by treatment with methanesulfonyl chloride in the presence of triethylamine or pyridine or p-toluenesulfonyl chloride in the presence of pyridine, respectively. The resulting sulfonate 8 can be treated with an alkalai metal azide, such as sodium or potassium azide in an aprotic dipolar solvent such as DMF or N-methylpyrrolidinone (NMP) with an optional catalyst such as 18-crown-6 at a temperature in the range of 50–90° C. to afford azide 9. The azide 9 can be reduced to the corresponding amine 10 by hydrogenation in the presence of a palladium, platinum or nickel catalyst, in an appropriate solvent such as ethyl acetate, THF, or methanol. Alternatively, azide 9 can be reduced to amine 10 by treatment with triphenylphosphine or other trivalent phosphorus compounds in a solvent such as THF, followed by addition of water. Amine 10 can also be prepared by treatment of the sulfonate 8 with potassium phthalimidate in DMF at 40–60° C. or in refluxing acetonitrile to afford the phthalimide 11, which is deprotected by treatment, for example, with aqueous methylamine in refluxing ethanol. A more direct route to amine 10 is to treat sulfonate 8 with aqueous ammonia solution in an isopropyl alcohol-THF solvent system in a sealed tube heated at 75–105° C. in an oil bath. Amine 10 is then acylated by reactions well-known to those skilled in the art to give (acylaminomethyl) oxazoldinones of structural formula 12. For example, amine 10 can be treated with an acid chloride or anhydride in the presence of a base such as pyridine or triethylamine at temperatures ranging from −40–40° C. to provide the acyl derivative 12. It can also be seen that other acyl derivatives, such as carbamates, can be prepared under similar reaction conditions. It can easily be seen that preparation of 12 provides an example of compounds of Structural Formula I. It can also be seen that in some cases, 12 can be transformed into other compounds of Structural Formula I by treatment with 40% aqueous formaldehyde in dimethyl sulfoxide at temperatures in the range of 90–150° C. optionally in the presence of an acid catalyst to afford the corresponding hydroxymethyl derivative 13.

Alternatively, compound 13 can be prepared by a less direct route, which offers the potential of providing other regioisomers that cannot be readily obtained by hydroxymethylation. As shown in Chart III, alkoxycarbonyl derivatives of 5-membered ring heterocycles, 14 (where m=number of methylenes), either available commercially or prepared by literature methods, can be treated with a nitrobenzene derivative 2 in a suitable solvent, such as DMSO, DMF, or the like, in the presence of a suitable base such as potassium carbonate at a suitable temperature in the range ambient to 90° C. to afford the biaryl derivative 15. The resulting nitro derivative is then reduced by catalytic hydrogenation in the presence of a suitable catalyst, such as palladium on carbon, W-2 Raney nickel, or platinum on sulfide carbon, in a suitable solvent, such as ethyl acetate, THF, methanol, or combinations thereof, to afford aniline derivative 16. When THF is used as solvent for this reduction, it is not necessary to remove the catalyst by filtration or to isolate aniline derivative 16, but merely to purge the reaction vessel with an inert gas such as nitrogen and add saturated sodium bicarbonate solution and treat the corresponding mixture with with either benzyl or methyl chloroformate for give the corresponding benzyl (R=$CH_2Ph$) or methyl (R=$CH_3$) carbamate derivatives 17. The ester group of either of the carbamate derivatives 17 can be reduced with either lithium borohydride or possibly with borane-THF complex to afford the corresponding alcohol 18. It can be seen by those skilled in the art that subsequent transformations of 18 will necessitate the protection of the hydroxyl group. This can be accomplished, for example, by preparation of the tert-butyldimethyl silyl (TBS) ether 19 (R=$Si(CH_3)_2t-Bu$) by treatment of 18 with tert-butyldimethylchlorosilane in the presence of a base such as imidazole or diisopropylethylamine, optionally in the presence of 4-dimethylaminopyridine as a catalyst, in a suitable solvent such as DMF, THF, or dichloromethane. Either of the carbamate derivatives 19 can be deprotonated with a lithium base such as lithium diisopropylamide (LDA) or lithium bis(trimethylsilyl)amide (LHMDS), in a suitable solvent such as THF, DMF or mixtures therof, at a suitable temperature, typically −78° C. to −40° C. to give a lithiated intermediate which is directly treated with (R)-(−)-glycidyl butyrate. Warming this reaction mixture to ambient or higher temperatures then affords the (hydroxymethyl)oxazoldinone 20 in highly enantiomerically enriched form.

Chart IV describes the conversion of (hydroxymethyl) oxazolidinone 20 into oxazolidinone antibacterial agents of Structural Formula I. As shown, compound 20 can be converted to the corresponding (acylaminomethyl) oxazoldinone 21 (R=straight or branched chain alkyl) by a sequence of reactions identical with that used to convert 7 to 12 in Chart II. (Acylaminomethyl)oxazolidinone 21 can then be deprotected by a number of methods, notably by treatment with methanolic HCl solution at reflux or by treatment with mixtures of acetic acid in THF-water at temperatures of 40–90° C. to afford alcohol 22. Alcohol 22 is an example of an oxazolidinone antibacterial agent of Structural Formula I. Further transformations outlined in Chart IV can be used to prepare other compounds of Structural Formula I from compound 22. As shown, alcohol 22 can be oxidized by treatment with reagents such as pyridinium dichromate in DMF or by treatment with oxgen gas in the presence of a noble metal catalyst in water solution or other methods known to thoses skilled in the art, to afford carboxylic acid 23. Carboxylic acid 23 can be esterified by treatment with an appropriate alkyl halide in the presence of a base such as potassium carbonate in an appropriate solvent, such as acetone, to give ester 24 (R=straight or branched chain alkyl). Alternatively, ester 24 can be obtained by addition of carboxylic acid 23 to a solution of gaseous HCl dissolved in an appropriate alcohol, or by other means known to those skilled in the art.

Chart V outlines methods by which alcohol 22 can be converted into other compounds of Structural Formula I. As shown, 22 can be converted into the corresponding mesylate (R=CH$_3$) or tosylate (R=p-CH$_3$C$_6$H$_4$) by treatment with methanesulfonyl chloride in the presence of triethylamine or pyridine or with p-toluenesulfonyl chloride in the presence of pyridine. The resulting sulfonate derivative 25 can be treated with an alkalai metal salt of a mercaptan (R=straight or branched chain alkyl or aryl) in an aprotic dipolar solvent such as DMF, DMSO, or acetonitrile with an optional catalyst such as 18-crown-6 at a temperature in the range of ambient to 90° C. to afford sulfide 26. Sulfide 26 can then be further transformed into either sulfoxide 27 or sulfone 28 by oxidation with appropriate stoichiometric amounts of a suitable oxidizing agent, such as m-chloroperoxybenzoic acid (MCPBA) in a suitable solvent such as dichloromethane, diethyl ether, or the like. Alternatively, sulfone 28 could be obtained directly by treatment with osmium tetroxide or ruthenium tetroxide in the presence of sodium periodate or by treatment with potassium hydrogen persulfate. Compounds 26, 27, and 28 constitute examples of compounds of Structural Formula I.

Other possible transformations of alcohol 22 are shown in Chart V. As shown, sulfonate derivative 25 can be treated with an alkalai metal azide in a dipolar aprotic solvent such as DMF, DMSO, acetonitrile or the like, optionally in the presence of a catalyst such as 18-crown-6, at a temperature in the range of 50–90° C. to afford azide 29. The azide 29 can then be reduced to the corresponding amine 30 by hydrogenation in the presence of a platinum, palladium, or nickel catalyst, in an appropriate solvent such as ethyl acetate, THF or methanol. Alternatively, azide 29 can be reduced by treatment with triphenylphoshine or other trivalent phosphorus compounds in a solvent such as THF, followed by addition of water. Amine 30 can then be used to form the corresponding sufonamide derivative 31 by treatment with an appropriate sulfonyl chloride (R=straight or branched chain alkyl, or aryl) in an appropriate solvent, such as pyridine. It can be seen that sulfonamide derivative 31 is an example of compounds of Structural Formula I.

Due to the shortage of commercially available 3-substituted heterocyclics in the pyrrole, pyrazole, or triazole series, some of the possible compounds of Structural formula I cannot be readily prepared by routes described in the previous Charts. As a result, the synthesis of these other heterocyclic oxazolidinone derivatives from aniline derivative 37 are described in Charts VI, VII, VIII, and IX.

The preparation of aniline derivative 37 is described in Chart VI. As shown, nitroaromatic 2 is treated with benzylamine in the presence of a suitable base, such as triethylamine or N,N-diisopropylethylamine, in a solvent such as acetonitrile, to afford displacement product 32. Nitro compound 32 can then be transformed into optically active oxazoldinone derivative 36 by methods used in Charts I and II to convert nitro derivative 3 into oxazolidinone 12. At this point in the synthesis, hydrogenolysis of 36 using palladium on carbon as catalyst and methanol as solvent serves to both remove the CbZ protecting group and the benzyl protecting group to give aniline 37.

Preparation of 3-substituted pyrrole derivatives can be accomplished as shown in Chart VI. Treatment of aniline 37 with the commercially available 3,5-dimethoxy-3-tetrahydrofurancarboxaldehyde under conditions of acid catalysis, such as in refluxing acetic acid, to afford 3-pyrrolecarboxaldehyde 38. Aldehyde 38 can then be transformed into other pyrrole analogs, such as hydroxymethyl pyrrole 39, ester 40, or oxime derivative 41 by methods well-known to those skilled in the art. It can be seen that pyrroles 30, 40 and 41 constitute examples of compounds of structural Formula I.

Transformation of aniline 37 into substituted triazole derivatives is described in Chart VII. As shown, diazotization of aniline 37 by treatment with nitrous acid, followed by addition of sodium azide, allows formation of azide 42 which is a useful precursor to formation of triazoles by means of a 1,3-dipolar cycloaddition with a substituted acetylene, 43. As shown, treatment of azide 42 with a substituted acetylene derivative 43 in a solvent such as benzene, toluene, and the like, at temperatures in the range of ambient to 120° C., optionally in the presence of a Lewis acid catalyst such as aluminum chloride, boron trifluoride etherate, titanium tetrachloride, or the like, affords the substituted triazole derivative 44. Alternatively, in the case where one of the R$^3$ groups of 43 is an acyl group, such as R$^4$CO in acetylene 45, the cycloaddition under the aforementioned conditions will give preferentially the 4-acyl triazole derivative 46 with lesser amounts of the corresponding 5-acyl triazole derivative 47. Alternatively, functionality permissible in R$^3$ of 44 can be used to transform 44 into acyl derivatives 46 and/or 47. 4-Acyl triazole oxazolidinone 46 can be transformed into oxime derivatives 48 or hydroxy compound 49 by methods known to those skilled in the art. It can be seen that 46, 48 and 49 constitute examples of compounds of structural Formula I.

Transformation of aniline 37 into both possible regioisomers of substituted pyrazole derivatives is shown in chart VIII. As shown, diazotization of aniline 37 followed by reduction of the diazonium salt with either tin [II] chloride or in-situ generated sodium sulfite gives the hyrazine derivative 50. It can be seen that hydrazine 50 can be reacted with triformylmethane, 51 (*Synthesis* 1989, 858), to form the pyrazole-4-carboxaldehyde 52, as shown. Alternatively, treatment of hydrazine 50 with 4-methoxy-2-oxo-but-3-enoic acid, ethyl ester, 53 (*Helv. Chim. Acta* 1967, 50, 128), will lead to the formation of the regioisomeric 3-carboethoxypyrazole 54. It can be seen that aldehyde 52 and ester 54 can be converted into other series of analogs by transformations described in Charts IV, V, and VI. It can be seen that 52 and 54 constitute examples of compounds of structural Formula I.

Examples of heteroaryl-phenyloxazolidinones which can be prepared as part of this invention are as follows:

(S)-N-[[3-[3-Fluoro-4-(1H-pyrrol-1-yl)phenyl]-2-oxo-5-oxazolidinyl]methyl]acetamide;

(S)-N-[[3-[3-Fluoro-4-(3-carbomethoxy-1H-pyrrol-1-yl) phenyl]-2-oxo-5-oxazolidinyl]methyl]acetamide;

(S)-N-[[3-[3-Fluoro-4-(1H-pyrrol-1-yl-3-carboxaldehyde) phenyl]-2-oxo-5-oxazolidinyl]methyl]acetamide;

(S)-N-[[3-[3-Fluoro-4-(3-(hydroxyiminomethyl)-1H-pyrrol-1-yl)phenyl]-2-oxo-5-oxazolidinyl]methyl] acetamide;

(S)-N-[[3-[3-Fluoro-4-(3-methoxyiminomethyl)-1H-pyrrol-1-yl)phenyl]-2-oxo-5-oxazolidinyl]methyl]acetamide;
(S)-N-[[3-[3-Fluoro-4-(3-hydroxymethyl-1H-pyrrol-1-yl)phenyl]-2-oxo-5-oxazolidinyl]methyl]acetamide;
(S)-N-[[3-[3-Fluoro-4-[3-(2-carboethoxyvinyl)-1H-pyrrol-1-yl)phenyl]-2-oxo-5-oxazolidinyl]methyl]acetamide;
(S)-N-[[3-[3-Fluoro-4-[3-(2-carboethoxyethyl)-1H-pyrrol-1-yl)phenyl]-2-oxo-5-oxazolidinyl]methyl]acetamide;
(S)-N-[[3-[3-Fluoro-4-[3-(3-hydroxypropyl)-1H-pyrrol-1-yl]phenyl]-2-oxo-5-oxazolidinyl]methyl]acetamide;
(S)-N-[[3-[3-Fluoro-4-[3-(3-methanesulfonylaminopropyl)-1H-pyrrol-1-yl]phenyl]-2-oxo-5-oxazolidinyl]methyl]acetamide;
(S)-N-[[3-[3-Fluoro-4-(1H-imidazol-1-yl)phenyl]-2-oxo-5-oxazolidinyl]methyl]acetamide;
(S)-N-[[3-[3-Fluoro-4-(4-methyl-1H-imidazol-1-yl)phenyl]-2-oxo-5-oxazolidinyl]methyl]acetamide;
(S)-N-[[3-[3-Fluoro-4-(4-ethyl-1H-imidazol-1-yl)phenyl]-2-oxo-5-oxazolidinyl]methyl]acetamide;
(S)-N-[[3-[3-Fluoro-4-[4-(carbomethoxy)-1H-imidazol-1-yl]phenyl]-2-oxo-5-oxazolidinyl]methyl]acetamide;
(S)-N-[[3-[3-Fluoro-4-[4-(hydroxymethyl)-1H-imidazol-1-yl]phenyl]-2-oxo-5-oxazolidinyl]methyl]acetamide;
(S)-N-[[3-[3-Fluoro-4-[4-(2-hydroxyethyl)-1H-imidazol-1-yl]phenyl]-2-oxo-5-oxazolidinyl]methyl]acetamide;
(S)-N-[[3-[3-Fluoro-4-[1H-imidazol-1-yl-4-carboxaldehyde]phenyl]-2-oxo-5-oxazolidinyl]methyl]acetamide;
(S)-N-[[3-[3-Fluoro-4-[3-(hydroxyiminomethyl)-1H-imidazol-1-yl]phenyl]-2-oxo-5-oxazolidinyl]methyl]acetamide;
(S)-N-[[3-[3-Fluoro-4-[3-(methoxyiminomethyl)-1H-imidazol-1-yl]phenyl]-2-oxo-5-oxazolidinyl]methyl]acetamide;
(S)-N-[[3-[3-Fluoro-4-(1H-pyazol-1-yl)phenyl]-2-oxo-5-oxazolidinyl]methyl]acetamide;
(S)-N-[[3-[3-Fluoro-4-(4-methyl-1H-pyrazole-1-yl)phenyl]-2-oxo-5-oxazolidinyl]methyl]acetamide;
(S)-N-[[3-[3-Fluoro-4-[3-(hydroxymethyl)-1H-pyrazole-1-yl]phenyl]-2-oxo-5-oxazolidinyl]methyl]acetamide;
(S)-N-[[3-[3-Fluoro-4-[3-(carbomethoxy)-1H-pyrazole-1-yl]phenyl]-2-oxo-5 -oxazolidinyl]methyl]acetamide;
(S)-N-[[3-[3-Fluoro-4-(1H-pyrazole-1-yl-3-carboxaldehyde)phenyl]-2-oxo-5-oxazolidinyl]methyl]acetamide;
(S)-N-[[3-[3-Fluoro-4-(3-(hydroxyiminomethyl)-1H-pyrazole-1-yl)phenyl]-2-oxo-5-oxazolidinyl]methyl]acetamide;
(S)-N-[[3-[3-Fluoro-4-(3-(methoxyiminomethyl)-1H-pyrazole-1-yl)phenyl]-2-oxo-5-oxazolidinyl]methyl]acetamide;
(S)-N-[[3-[3-Fluoro-4-[4-(hydroxymethyl)-1H-pyrazole-1-yl]phenyl]-2-oxo-5-oxazolidinyl]methyl]acetamide;
(S)-N-[[3-[3-Fluoro-4-[4-(carbomethoxy)-1H-pyrazole-1-yl]phenyl]-2-oxo-5-oxazolidinyl]methyl]acetamide;
(S)-N-[[3-[3-Fluoro-4-(1H-pyrazole-1-yl-4-carboxaldehyde)phenyl]-2-oxo-5-oxazolidinyl]methyl]acetamide;
(S)-N-[[3-[3-Fluoro-4-(4-(hydroxyiminomethyl)-1H-pyrazole-1-yl)phenyl]-2-oxo-5-oxazolidinyl]methyl]acetamide;
(S)-N-[[3-[3-Fluoro-4-(4-(methoxyiminomethyl)-1H-pyrazole-1-yl)phenyl]-2-oxo-5-oxazolidinyl]methyl]acetamide;
(S)-N-[[3-[3-Fluoro-4-(1H-1,2,4-triazol-1-yl)phenyl]-2-oxo-5-oxazolidinyl]methyl]acetamide;
(S)-N-[3-[3-Fluoro-4-[3-mercapto-4H-1,2,4-triazol-4-yl]phenyl]-2-oxo-5-oxazolidinyl]methylacetamide;
(S)-N-[3-[3-Fluoro-4-[3-methylthio-4H-1,2,4-triazol-4-yl]phenyl]-2-oxo-5-oxazolidinyl]methylacetamide;
(S)-N-[3-[3-Fluoro-4-[4H-1,2,4-triazol-4-yl]phenyl]-2-oxo-5-oxazolidinyl]methylacetamide;
(S)-N-[[3-[3-Fluoro-4-(1H-1,2,3-triazol-1-yl)phenyl]-2-oxo-5-oxazolidinyl]methyl]acetamide;
(S)-N-[[3-[3-Fluoro-4-(4-carbomethoxy-1H-1,2,3-triazol-1-yl)phenyl]-2-oxo-5-oxazolidinyl]methyl]acetamide;
(S)-N-[[3-[3-Fluoro-4-(4-(hydroxymethyl)-1H-1,2,3-triazol-1-yl)phenyl]-2-oxo-5-oxazolidinyl]methyl]acetamide;
(S)-N-[[3-[3-Fluoro-4-(4-(1-hydroxyethyl)-1H-1,2,3-triazol-1-yl)phenyl]-2-oxo-5-oxazolidinyl]methyl]acetamide;
(S)-N-[[3-[3-Fluoro4-(1H-1,2,3-triazol-1-yl-4-carboxaldehyde)phenyl]-2-oxo-5-oxazolidinyl]methyl]acetamide;
(S)-N-[[3-[3-Fluoro-4-(4-(hydroxyiminomethyl)-1H-1,2,3-triazol-1-yl)phenyl]-2-oxo-5 -oxazolidinyl]methyl]acetamide, oxime;
(S)-N-[[3-[3-Fluoro-4-(4-(methoxyiminomethyl)-1H-1,2,3-triazol-1-yl)phenyl]-2-oxo-5-oxazolidinyl]methyl]acetamide;
(S)-N-[[3-[3-Fluoro-4-(4-acetyl-1H-1,2,3-triazol-1-yl)phenyl]-2-oxo-5-oxazolidinyl]methyl]acetamide;
(S)-N-[[3-[3-Fluoro-4-(4-(1-hydroxyiminoethyl)-1H-1,2,3-triazol-1-yl)phenyl]-2-oxo-5-oxazolidinyl]methyl]acetamide;
(S)-N-[[3-[3-Fluoro-4-(4-(1-methoxyiminoethyl)-1H-1,2,3-triazol-1-yl)phenyl]-2-oxo-5-oxazolidinyl]methyl]acetamide;
(S)-N-[[3-[3-Fluoro-4-(2H-1,2,3-triazol-2-yl)phenyl]-2-oxo-5-oxazolidinyl]methyl]acetamide;
(S)-N-[[3-[3-Fluoro-4-(1H-1,2,3,4-tetrazol-1-yl)phenyl]-2-oxo-5-oxazolidinyl]methyl]acetamide;
(S)-N-[[3-[3-Fluoro-4-(2H-1,2,3,4-tetrazol-2-yl)phenyl]-2-oxo-5-oxazolidinyl]methyl]acetamide;
(S)-N-[[3-[3-Fluoro-4-(1H-indol-1-yl)phenyl]-2-oxo-5-oxazolidinyl]methyl]acetamide;
(S)-N-[[3-[3-Fluoro-4-(7-aza-1H-indol-1-yl)phenyl]-2-oxo-5-oxazolidinyl]methyl]acetamide;
(S)-N-[[3-[3-Fluoro-4-(1H-benzimidazol-1-yl)phenyl]-2-oxo-5-oxazolidinyl]methyl]acetamide;
(S)-N-[[3-[3-Fluoro-4-(1H-indazol-1-yl)phenyl]-2-oxo-5-oxazolidinyl]methyl]acetamide;
(S)-N-[[3-[3-Fluoro-4-(1H-benzotriazol-1-yl)phenyl]-2-oxo-5-oxazolidinyl]methyl]acetamide; and
(S)-N-[[3-[3-Fluoro-4-(1H-1,2,3-triazolo[4,5b]-pyridin-1-yl)phenyl]-2-oxo-5-oxazolidinyl]methyl]acetamide.

Antibacterial Activity

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as desribed in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. The activity of selected compounds of this invention against *Staphylococcus aureus* and *Streptococcus pneumoniae* are shown in Table 1.

TABLE 1

In vitro Activities: Minimum Inhibitory Concentrations (µg/mL)

| Example No. | S. aureus, UC ®9213 | S. pneumoniae, UC ®9912 |
|---|---|---|
| 1 | <0.5 | <0.5 |
| 2 | 2 | 1 |
| 3 | 2 | <0.5 |
| 4 | 4 | 1 |
| 5 | 4 | 1 |
| 6 | 1 | <0.5 |
| 7 | 1 | <0.5 |
| 8 | 4 | 1 |
| 9 | >32 | 8 |
| 10 | 8 | 1 |
| 11 | >16 | 1 |
| 12 | 0.25 | <0.06 |
| 13 | 1 | 0.25 |
| 14 | 2 | 0.25 |
| 15 | 1 | 0.25 |
| 16 | 1 | <0.25 |
| 17 | 1 | 0.5 |
| 18 | 4 | 0.5 |
| 19 | 4 | 0.5 |
| 20 | 4 | 1 |
| 21 | 0.5 | 0.25 |
| 22 | 8 | 0.5 |
| 23 | 4 | 0.5 |
| 24 | 4 | 0.5 |
| 25 | 4 | 0.5 |
| 26 | 8 | 0.5 |
| Vancomycin | 1 | 0.5 |

Antimicrobial activity was tested in vivo using the Murine Assay procedure. Groups of female mice (six mice of 18–20 grams each) were injected intraperitoneally with bacteria which were thawed just prior to use and suspended in brain heart infusion with 4% brewers yeast UC9213 (*Staphylococcus aureus*) or brain heart infusion (Streptococcus species). Antibiotic treatment at six dose levels per drug was administered one hour and five hours after infection by either oral intubation or subcutaneous ("subcut.") routes. Survival was observed daily for six days. $ED_{50}$ values based on mortality ratios were calculated using probit analysis. The subject compounds were compared against a well-known antimicrobial (Vancomycin) as a control. The data are shown in Table 2.

TABLE 2

In vivo Activities: $ED_{50}$(mg/Kg)

| Example No. | S. aureus, UC ®9213 | Control, $ED_{50}$ |
|---|---|---|
| 3 | 9.5 | vancomycin, 2.2 |
| 4 | 5.7 | vancomycin, 2.4 |
| 6 | 4.7 | vancomycin, 2.0 |
| 7 | 11.9 | vancomycin, 1.2 |
| 15 | 7.3 | — |
| 16 | 5.5 | — |

EXAMPLES

Example 1

(S)-N-[[3-[3-Fluro-4-(1H-pyrrol-1-yl)phenyl]-2-oxo-5-oxazolidinyl]methyl]acetamide
3-Fluoro-1-nitro-4-(1H-pyrrol-1-yl)benzene:

A slurry of 403 mg (630 mg of 60% in oil, 15.75 mmol) of sodium hydride in 85 mL THF was treated with 1.01 g (1.04 mL, 15 mmol) of pyrrole, followed by warming at 50° C. foe 15 min. The solution was then treated with 2.51 g (1.74 mL, 15.75 mmol) of 3,4-difluoronitrobenzene, followed by warming at reflux for 18 h. The mixture was then cooled and treated with 10 mL saturated ammonium chloride solution. The mixture was diluted with ethyl acetate and extracted with water (2x). Drying ($Na_2SO_4$) and concentration in vacuo afforded a dark brown solid, which was chromatographed over 75 g of 230–400 mesh silica gel, eluting with 30% (v/v) dichloromethane in hexane. These procedures afforded 2.05 g (66%) of the title pyrrole derivative as a light yellow solid. $^1H$ NMR ($CDCl_3$): δ 8.14, 7.57, 7.16, 6.44.

3-Fluoro-1-(phenylmethoxycarbonylamino)-4-(1H-pyrrol-1-yl)benzene

A solution of 500 mg (2.43 mmol) of the previous pyrrole derivative in 50 mL of 4:1 THF-water was treated with 75 mg of 5% platinum on sulfide carbon followed by hydrogenation at one atmosphere for 18 h. The mixture was then treated with 10 mL saturated $NaHCO_3$ solution and cooled to −20° C. The mixture was treated with 477 mg (0.42 mL, 2.79 mmol) of benzyl chloroformate followed by warming to ambient temperature for 48 h. The mixture was filtered through celite, washing the filter cake with methanol. The mixture was concentrated to ca. half the original volume, and the mixture was diluted with ethyl acetate and extracted with water (4x) and saturated NaCl solution. Drying ($Na_2SO_4$) and concentration in vacuo afforded a brown solid, which was chromatographed over 35 g 230–400 mesh silica gel, eluting with 1:3:32 methanol-dichloromethane-hexane, and then with 1:3:16 methanol-dichloromethane-hexane. These procedures afforded 581 mg of the title CBZ derivative as a brown solid, suitable for use in the next step. $^1H$ NMR ($CDCl_3$): 7.50, 7.40, 7.30, 7.09, 6.98, 6.35, 5.23.

(S)-[3-[3-Fluoro-4-(1H-pyrrol-1-yl)phenyl]-2-oxo-5-oxazolidinyl]methanol

A solution of 300 mg (0.97 mmol) of CBZ derivative 2 in 5 mL THF at −78° C. was treated with 1.06 mL (1.0M, 1.06 mmol) of lithium bis(trimethylsilyl)amide followed by stirring at −78° C. for 30 min. The solution was treated with 153 mg (0.15 mmol) of (R)-(−)-glycidiyl butyrate followed by warming to 0° C. and then gradual warming to ambient temperature for 48 h. The mixture was diluted with ethyl acetate and extracted with water and saturated NaCl solution. Drying ($Na_2SO_4$) and concentration in vacuo afforded a red-brown oil which was subjected to radial chromatography on a 2 mm chromatotron plate, eluting with 2% (v/v) methanol in dichloromethane and then with 5% (v/v) methanol in dichloromethane. These procedures afforded 157 mg (59%) of the title oxazoldinone as a light tan solid. High Resolution Mass Spectrum: Calculated For $C_{14}H_{13}FN_2O_3$: 276.0910. Found: 276.0918.

(S)-[3-[3-Fluoro-4-(1H-pyrrol-1-yl)phenyl]-2-oxo-5-oxazolidinyl]methyl azide

A solution of 1.94 g (7.0 mmol) of the previous alcohol and 1.24 g (1.71 mL, 12.25 mmol) of triethylamine in 60 mL dichloromethane at 0° C. was treated with 1.0 g (0.68 mL, 8.78 mmol) of methanesulfonyl chloride, followed by stirring at 0° C. for 30 min. The solution was warmed to ambient temperature and diluted with dichloromethane, followed by extraction with water (3x) and saturated NaCl solution. Drying ($Na_2SO_4$) and concentration in vacuo afforded an amber oil which was dissolved in 120 mL DMF, treated with 4.5 g (70 mmol) of sodium azide and warmed at 60° C. for 18 h. The mixture was cooled and diluted with 75 mL of 1:1 ether-ethyl acetate and extracted with water (6x40 mL). Drying ($Na_2SO_4$) and concentration in vacuo afforded 2.13 g (100%) of the title azide as a yellow-brown solid, sufficiently pure for use in the next step. High Resolution Mass Spectrum: Calculated For $C_{14}H_{12}FN_5O_2$: 302.1053. Found: 302.1056.

(S)-N-[[3-[3-Fluro-4-(1H-pyrrol-1-yl)phenyl]-2-oxo-5-oxazolidinyl]methyl]acetamide A solution of 1.0 g (3.32 mmol) of the previous azide in 30 mL methanol and 15 mL THF was treated with 200 mg of platinum on sulfide carbon followed by hydrogenation at one atmosphere for 24 h. The solution was filtered though celite, washing the filter cake with THF. The filtrate was concentrated in vacuo and the residue was dissolved in pyridine and treated with acetic anydride followed by stirring at ambient temperature for 48 h. The solution was concentrated under high vacuum, and the brown solid obtatined was dissolved in ethyl acetate and extracted with water (2×). Drying ($Na_2SO_4$) and concentration in vacuo afforded a brown solid which was chromatographed over 50 g of 230–400 mesh silica gel, eluting with 1% (v/v) methanol in dichloromethane and then with 2% (v/v) methanol in dichloromethane. These procedures afforded 582 mg (56%) of the title compound as an off-white solid, mp 198–199.5° C. High Resolution Mass Spectrum: Calculated For CHFNO: 317.1176. Found: 317.1182.

Example 2

(S)-N-[[3-[3-Fluoro-4-(1H-pyrazol-1-yl)phenyl]-2-oxo-5-oxazolidinyl]methyl]acetamide:
3-Fluoro-1-nitro-4-(1H-pyrazol-1-yl)benzene A solution of 2.0 g (29.37 mmol) of pyrazole and 8.12 g (58.75 mmol) of potassium carbonate in 70 mL of DMSO was treated with 4.67 g (3.25 mL, 29.37 mmol) of 3,4-difluoronitrobenzene followed by warming at 90° C. for 18 h. The solution was cooled and diluted with 100 mL water and was extracted with ethyl acetate (2×100 mL). The organic layers were extracted with water (5×100 mL) and with saturated NaCl solution (75 mL). Drying ($Na_2SO_4$) and concentration in vacuo afforded an off-white solid which was recrystallized from hot hexanes to afford 5.3 g (87%) of the title pyrazole derivative as an off-white solid, mp 128–129° C.

3-Fluoro-1-(phenylmethoxycarbonylamino)-4-(1H-pyrazol-1-yl)benzene

A solution of the previously prepared pyrazole in 120 mL THF was treated with 1.5 g of W-2 Raney Nickel followed by hydrogenation under 40 psi of hydrogen for 16 h. The solution was filtered through celite, washing the filter cake with acetone, and concentration of the filtrate in vacuo. The yellow residue obtained was dissolved in 100 mL THF and treated with 75 mL saturated $NaHCO_3$ solution, followed by cooling to 0° C. The solution was then treated with 7.30 g (42.72 mmol) of benzyl chloroformate followed by stirring at 0° C. for 30 min and then by warming to ambient temperature for 1 h. The mixture was diluted with 125 mL ethyl acetate and 100 mL water. The layers were separated and the aqueous layer was extracted with 100 ml ethyl acetate. The combined organic layers were extracted with saturated $NaHCO_3$ solution (2×100 mL) and saturated NaCl solution. Drying ($Na_2SO_4$) and concentration in vacuo afforded a light beige solid, which was recrystallized from chloroform-hexane to afford 5.92 g (79%) of the title compound as glistening white plates, mp 82–83° C.

(S)-[3-[3-fluoro-4-(1H-pyrazol-1-yl)phenyl]-2-oxo-5-oxazolidinyl]methanol

A solution of 3.0 g (9.63 mmol) of the CBZ derivative 2 in 130 mL THF at −78° C. was treated with 10.6 mL (1.0M, 10.60 mmol) of lithium bis(trimethylsilyl)amide in THF followed by stirring at −78° C. for 30 min. The solution was then treated with 1.53 g (1.50 mL, 10.60 mmol) of neat (R)-(−)-glycidiyl butyrate, followed by stirring at −78° C. for 30 min and then warming to ambient temperature for 18 h. The mixture was treated with 2 mL saturated ammonium chloride solution, followed by dilution with 400 mL ethyl acetate. The mixture was extracted with water (2×100 mL) and saturated NaCl solution (200 mL). Drying ($Na_2SO_4$) and concentration in vacuo afforded a yellow solid which was recrystallized from hot methanol to afford 2.28 g (85%) of compound 3 as fine white needles, mp 180–181° C.

(S)-[3-[3-Fluoro-4-(1H-pyrazol-1yl)phenyl]-2-oxo-5-oxazolidinyl]methyl methanesulfonate A slurry of 403 mg (1.45 mmol) of the previously prepared compound and 882 mg (1.22 mL, 8.71 mmol) of triethylamine in 15 mL dichloromethane at 0° C. was treated with 500 mg (0.34 ml, 4.36 mmol) of methanesulfonyl chloride dropwise. The solution was stirred at 0° C. for 30 min, followed by warming to ambient temperature. The mixture was diluted with 20 mL dichloromethane and extracted with water (2×25 mL) and saturated $NaHCO_3$ solution. Drying ($Na_2SO_4$) and concentration in vacuo afforded 520 mg (ca. 100%) of the title mesylate, sufficiently pure for further use. $^1$H NMR (DMSO-$d_6$): δ 8.16, 7.80, 7.48, 6.55, 5.05, 4.53, 4.23, 3.89, 3.25.

(S)-[3-[3-Fluoro-4-(1H-pyrazol-1yl)phenyl]-2-oxo-5-oxazolidinyl]methylazide

A solution of 518 mg (1.45 mmol) of the previous mesylate in 15 mL N, N-dimethylformamide was treated with 1.89 g (29.07 mmol) of sodium azide followed by warming at 70° C. for 48 h. The mixture was diluted with 100 mL ethyl acetate followed by extraction with water (6×75 mL) and saturated NaCl solution (75 mL). Drying ($Na_2SO_4$) and concentration in vacuo afforded a beige solid which was chromatographed over 50 g of 230–400 mesh silica gel, eluting with 3% (v/v) acetone in dichloromethane and then with 3.5% (v/v) methanol in dichloromethane. These procedures afforded 355 mg (81%) of the title azide as a white solid. $^1$H NMR ($CDCl_3$): δ 7.99, 7.92, 7.76, 7.24, 6.49, 4.83, 4.12, 3.99, 3.74, 3.62.

(S)-N-[[3-[3-Fluoro-4-(1H-pyrazol-1-yl)phenyl]-2-oxo-5-oxazolidinyl]methyl]acetamide A solution of 355 mg of the previous azide in 30 mL ethyl acetate was treated with 150 mg of palladium on calcium carbonate followed by hydrogenation at one atmosphere for 18 h. The solution was then treated with 15 mL pyridine and 10 mL acetic anhydride followed by stirring at ambient temperature for 18 h. The mixture was diluted with 100 mL ethyl acetate and filtered through celite, washing the filter cake with ethyl acetate. The mixture was concentrated in vacuo, and the remaining pyridine and acetic anhydride removed by short path distillation under high vacuum (0.2 mmHg/hot water bath). The solid residue obtained was recrystallized from hot acetone-hexane to afford 192 mg (51%) of the title compound as a white solid, mp 183–184° C.

Example 3

(S)-N-[[3-[3-Fluoro-4-(1H-imidazol-1-yl)phenyl]-2-oxo-5-oxazolidinyl]methyl]acetamide
3-Fluoro-4-(1H-imidazol-1-yl)nitrobenzene A solution of 2.14 g (31.4 mmol) of imidazole and 10.9 g (62.8 mmol) of dibasic potassium phosphate in 190 mL DMSO was treated with 5.25 g (3.7 mL, 32.9 mmol) of 3,4-difluoronitrobenzene followed by warming at 90° C. for 18 h. The solution was diluted with ethyl acetate and was extracted with water. The water layer was back-extracted with ethyl acetate and the combined organic layers were then extracted with water (2×). The organic layer was dried ($Na_2SO_4$) and concentrated in vacuo to afford a brown solid. This material was chromatographed over 250 g of 230–400 mesh silica gel, eluting with dichloromethane, and then with 1% (v/v) methanol in dichloromethane, and finally with 2% (v/v) methanol in dichloromethane. These procedures afforded 6.0 g (92%) of the title compound as a bronze colored solid. $^1$H NMR (CDCl$_3$): δ 8.17, 7.96, 7.63, 7.35, 7.26.

3-Fluoro-4-(1H-imidazol-1-yl)-1-(phenylmethoxycarbonylamino)benzene

A solution of 500 mg (2.41 mmol) of the previous nitro compound in 50 mL THF was treated with 100 mg of 10% palladium on carbon, followed by hydrogenation at atmospheric pressure for 20 h. The mixture was treated with 60 mg of additional 10% palladium on carbon and hydrogenation at atmospheric pressure was continued for 5 h. The mixture was then filtered through celite washing the filter cake with methanol. The filtrate was concentrated in vacuo to afford a brown oil, which was dissolved in 50 mL anhydrous THF, followed by treatment with 405 mg (4.82 mmol) of solid sodium bicarbonate. The solution was cooled to −20° C., followed by addition of 493 mg (0.43 mL, 2.89 mmol) of benzyl chloroformate dropwise. The mixture was warmed to ambient temperature for 18 h, followed by dilution with ethyl acetate. The solution was extracted with water (3×) and saturated sodium chloride solution. Drying (Na$_2$SO$_4$) and concentration in vacuo afforded a light brown solid which was recrystallized from hot chloroform-hexane to afford 692 mg (92%) of the title compound as light brown crystals. High Resolution Mass Spectrum: Calculated for C$_{17}$H$_{14}$FN$_3$O$_2$: 311.1070. Found: 311.1092.

(S)-[3-[3-Fluoro-4-(1H-imidazol-1-yl)phenyl]-2-oxo-5-oxazolidinyl]methanol

A solution of 500 mg (1.61 mmol) of the previous CBZ derivative in 22 mL THF and 4 mL DMF at −78° C. was treated with 1.69 mL (1.69 mmol) of lithium bis(trimethylsilyl)amide followed by stirring at −78° C. for 20 min. The solution was treated with 243 mg (0.24 mL, 1.69 mmol) of (R)-(−)-glycidyl butyrate followed by warming to 0° C. and then to ambient temperature. After stirring 3 h at ambient temperature, TLC evidence suggested that no reaction had occurred. The solution was then warmed at 40° C. for 2 h, followed by cooling and stirring at ambient temperature for 18 h. The solution was then diluted with ethyl acetate and extracted with water (3×). Drying (Na$_2$SO$_4$) and concentration in vacuo afforded a brown solid. This material was chromatographed over 40 g of 230–400 mesh silica gel eluting with 2% (v/v) methanol in dichloromethane and then with 5% (v/v) methanol in dichloromethane. These procedures afforded 214 mg (48%) of the title compound as a light yellow solid. High Resolution Mass Spectrum: Calculated For C$_{13}$H$_{12}$FN$_3$O$_3$: 277.0863. Found: 277.0876.

(S)-[3-[3-Fluoro-4-(1H-imidazol-1-yl)phenyl]-2-oxo-5-oxazolidinyl]methylazide

A solution of 150 mg (0.54 mmol) of the previous oxazolidinone and 96 mg (0.13 mL, 0.95 mmol) of triethylamine in 5 mL dichloromethane at 0° C. was treated with 77 mg (52 μL, 0.68 mmol) of methanesulfonyl chloride, followed by stirring at 0° C. for 30 min. The solution was warmed to ambient temperature followed by dilution with dichloromethane and extraction with water (3×). Drying (Na$_2$SO$_4$) and concentration in vacuo afforded a light brown foam. This material was dissolved in 10 mL DMF and treated with 525 mg (8.1 mmol) of sodium azide, followed by warming at 60° C. for 48 h. The solution was cooled and diluted with ethyl acetate followed by extraction with water (3×). Drying (Na$_2$SO$_4$) and concentration in vacuo afforded 163 mg (100%) of the title azide as a yellow oil. $^1$H NMR (CDCl$_3$): δ 8.15, 7.74, 7.46, 7.35, 7.29, 4.85, 4.12, 3.90, 3.76, 3.59.

(S)-N-[[3-[3-Fluoro-4-(1H-imidazol-1-yl)phenyl]-2-oxo-5-oxazolidinyl]methyl]acetamide A solution of 163 mg (0.54 mmol) of the azide in 8 mL pyridine was treated with 85 mg of palladium on calcium carbonate and 110 mg (0.10 mL, 1.08 mmol) of acetic anhydride. This mixture was hydogenated at one atmosphere for 20 h. The mixture was then treated with 80 mg of palladium on calcium carbonate followed by hydrogenation at one atmosphere for 4 h. The solution was filtered through celite, washing the filter cake with ethyl acetate. The filtrate was concentrated under high vacuum, and the residue was subjected to radial chromatography on a 2 mm chromatotron plate eluting with 2% (v/v) methanol in dichloromethane and then with 5% (v/v) methanol in dichloromethane. These procedures afforded 84 mg (49%) of the title compound as a white solid. High Resolution Mass Spectrum: Calculated For C$_{15}$H$_{15}$FN$_4$O$_3$: 318.1128. Found: 318.1140.

Example 4

(S)-N-[[3-[3-Fluoro-4-(1H-1,2,4-triazol-1-yl)phenyl]-2-oxo-5-oxazolidinyl]methyl]acetamide 3-Fluoro-1-nitro-4-(1H-1,2,4-triazol-1-yl)benzene A solution of 5.0 g (72.4 mmol) of 1H-1,2,4-triazole and 25.22 g (144.8 mmol) of dibasic potassium phosphate in 150 mL DMSO was treated with 11.52 g (72.4 mmol) of 3,4-difluoronitrobenzene followed by warming at 90° C. for 3 h. The solution was cooled and added to 500 mL water, and the resulting white solid was collected by filtration and washed with water. The white solid obtained was dried in vacuo (60° C./10 mmHg) to afford 10.79 g (72%) of the title compound as a white solid. High Resolution Mass Spectrum: Calculated for C$_8$H$_5$FN$_4$O$_2$: 208.0396. Found: 208.0408.

3-Fluoro-4-(1H-1,2,4-triazol-1-yl)aniline

A solution of 8.7 g (41.83 mmol) of the previous nitro compound in 350 mL of 1:1 methanol-THF was treated with 3.5 g of 10% palladium on carbon followed by hydrogenation under 45 psi of hydrogen pressure for 18 h. The solution was filtered through celite, washing the filter cake with methanol. The filtrate was concentrated in vacuo and the residue obtained was chromatographed over 200 g of 230–400 mesh silica gel eluting with 1% (v/v) methanol in dichloromethane and then with 3% (v/v) methanol in dichloromethane. These procedures afforded 4.0 g (54%) of the aniline derivative as an off-white solid. High Resolution Mass Spectrum: Calculated for C$_8$H$_7$FN$_4$: 178.0655. Found: 178.0673.

3-Fluoro-1-(phenylmethoxycarbonylamino)-4-(1H-1,2,4-triazol-1-yl)benzene

A solution of 4.0 g (22.5 mmol) of the previous aniline derivative in 50 mL acetone was treated with 50 mL of saturated NaHCO$_3$ solution, followed by cooling to 0° C. The solution was treated with 8.0 g (6.78 mL, 47.26 mmol) of benzyl chloroformate. The solution was warmed to ambient temperature for 1 h, followed by addition to 300 mL water and extraction with ethyl acetate (2×300 mL). The organic layer was extracted with 300 mL water and dried (Na$_2$SO$_4$). Concentration in vacuo afforded a beige solid which was recrystallized from chloroform-hexane to afford 2.6 g (37%) of the title CBZ derivative. High Resolution Mass Spectrum: Calculated for C$_{16}$H$_{13}$FN$_4$O$_2$: 312.1022. Found: 312.1033.

(S)-[3-[3-Fluoro-4-(1H-1,2,4-triazol-1-yl)phenyl]-2-oxo-5-oxazolidinyl]methanol

A solution of 2.5 g (8.0 mmol) of the previously prepared CBZ derivative in 115 mL THF at −78° C. was treated with 8.8 mL (1.0M, 8.8 mmol) of lithium bis(trimethylsilyl)amide, followed by stirring at −78° C. for 30 min. The solution was then treated with 1.27 g (1.25 mL, 8.8 mmol) of (R)-(-)-glycidiyl butyrate, followed by stirring at -78° C. for 15 min. The solution was then warmed to ambient temperature for 18 h. The mixture was treated with 2 mL saturated ammonium chloride solution, followed by dilution with 100 ml water and extraction with ethyl acetate (2×100 mL). Drying (Na$_2$SO$_4$) and concentration in vacuo afforded a semi-solid, which was triturated with chloroform to provide 1.4 g (57%) of the title oxazolidinone. High Resolution Mass Spectrum: Calculated for C$_{12}$H$_{11}$FN$_4$O$_3$: 278.0815. Found: 278.0836.

(S)-[3-[3-Fluoro-4-(1H-1,2,4-triazol-1-yl)phenyl]-2-oxo-5-oxazolidinyl]methylazide A slurry of 1.0 g (3.6 mmol) of the previously prepared oxazolidinone and 548 mg (0.76 mL, 5.42 mmol) of triethylamine in 20 mL dichloromethane at 0° C. was treated with 495 mg (0.33 mL, 4.32 mmol) of methanesulfonyl chloride. The solution was then warmed to ambient temperature for 2 h. The solution was then treated with 20 mL water and the layers separated. The organic layer was dried (Na$_2$SO$_4$) and concentrated in vacuo to afford 1.0 g (75%) of the the intermediate mesylate as a tan solid. A soution of 1.34 g (3.6 mmol) of this material and 2.34 g (36 mmol) of sodium azide in 36 mL of DMF was warmed at 70° C. for 18 h. The solution was cooled and diluted with 100 mL ethyl acetate, followed by extraction with water (5×75 mL). Drying (Na$_2$SO$_4$) and concentration in vacuo afforded 1 g (88%) of the title azide as an off-white solid. $^1$H NMR Spectrum (CDCl$_3$): δ 8.65, 8.13, 7.91, 7.83, 7.32, 4.85, 4.14, 3.92, 3.77, 3.63.

(S)-N-[[3-[3-Fluoro-4-(1H-1,2,4-triazol-1-yl)phenyl]-2-oxo-5-oxazolidinyl]methyl]acetamide A solution of 100 mg (0.36 mmol) of the azide in 3 ml pyridine was treated with 50 mg of palladium on calcium carbonate followed by hydrogenation at one atmosphere for 18 h. The solution was treated with 0.2 mL acetic anhydride followed by stirring at ambeient temperature for 18 h. The solvent was removed in vacuo and the residue dissolved in ethyl acetate and extracted with water. The organic layer was dried (Na$_2$SO$_4$) and concentrated in vacuo to afford a light beige solid. This material was subjected to radial chromatography on a 2 mm plate eluting with 2% (v/v) methanol in dichloromethane and then with 4% (v/v) methanol in dichloromethane. These procedures afforded 62 mg (54%) of the title compound as a white solid. High Resolution Mass Spectrum: Calculated for C$_{14}$H$_{14}$FN$_5$O$_3$: 319.1018. Found: 319.1087.

Example 5

(S)-N-[[3-[3-Fluoro-4-(1H-indol-1-yl)phenyl]-2-oxo-5-oxazolidinyl]methyl]acetamide
3-Fluoro-4-(1H-indol-1-yl)nitrobenzene A slurry of 334 mg (374 mg of 60% in oil, 9.35 mmol) of sodium hydride in 5 mL THF was treated with a solution of 1.0 g (8.5 mmol) of indole in 5 mL THF, followed by stirring at ambient temperature for 15 min. The solution was then treated with 1.35 g (8.5 mmol) of 3,4-difluoronitrobenzene. The solution was stirred at ambient temperature for 48 h, followed by concentration in vacuo to afford brown oil which was dissolved in ethyl acetate and washed with water. Drying (Na$_2$SO$_4$) and concentration in vacuo afforded an oil which was chromatographed over 100 g of 230–400 mesh silica gel, eluting with 20% (v/v) ethyl acetate in hexane. These procedures afforded 1.1 g (51%) of the title compound as a yellow solid. $^1$H NMR (CDCl$_3$): δ 8.23, 7.74, 7.40, 7.35, 7.30, 6.80.

3-Fluoro-4-(1H-indole-1-yl)-1-(phenylmethoxycarbonylamino)benzene

A solution of 1.0 g (3.9 mmol) of the previously prepared nitro compound in 5 mL THF was treated with 200 mg of W-2 Raney nickel followed by hydrogenation at one atmosphere for 18 h. The solution was filtered through celite, washing the filter cake with THF. The filtrate was concentrated in vacuo and the residue dissolved in 10 mL acetone and treated with 8.2 mL saturated NaHCO$_3$ solution, followed by cooling to 0° C. and addition of 699 mg (4.1 mmol) of benzyl chloroformate. The solution was warmed to ambient temperature for 18 h, diluted with ethyl acetate and extracted with water. Drying (Na$_2$SO$_4$) and concentration in vacuo afforded an oil, which was chromatographed over 75 g of 230–400 mesh silica gel, eluting with 50% (v/v) ethyl acetate in hexane. These procedures afforded 1.03 g (71%) of the title compound as a yellow solid. $^1$H NMR (CDCl$_3$): δ 7.69, 7.60, 7.40, 7.25, 7.15, 6.70.

(S)-[3-[3-Fluoro-4-(1H-indol-1-yl)phenyl]-2-oxo-5-oxazolidinyl]methanol

A solution of 1.0 g (2.77 mmol) of the previous CBZ derivative in 5 mL THF at -78° C. was treated with 3.05 mL (1.0M, 3.05 mmol) of lithium bis(trimethylsilyl)amide in THF followed by stirring at -78° C. for 45 min. The solution was treated with 440 mg (0.43 mL, 3.05 mmol) of (R)-(-)-glycidiyl butyrate followed by stirring at -78° C. for 15 min, warming to 0° C. for 15 min and finally warming to ambient temperature for 18 h. The mixture was diluted with ethyl acetate and extracted with water. Drying (Na$_2$SO$_4$) and concentration in vacuo afforded a semisolid which was chromatographed over 60 g of 230–400 mesh silica gel, eluting with 2% (v/v) methanol in dichloromethane. These procedures afforded 630 mg (70%) of the title compound as a white solid. $^1$H NMR (CDCl$_3$): δ 7.69, 7.50, 7.38, 7.25, 6.71, 4.80, 4.09, 3.79.

(S)-[3-[3-Fluoro-4-(1H-indol-1-yl)phenyl]-2-oxo-5-oxazolidinyl]methylazide

A solution of 484 mg (1.2 mmol) of the previous mesylate in 10 mL DMF was treated with 390 mg (6 mmol) of sodium azide followed by warming at 90° C. for 18 h. The solution was cooled and diluted with ethyl acetate and extracted with water. Drying (Na$_2$SO$_4$) and concentration in vacuo afforded 336 mg (80%) of the title azide as a gum, sufficiently pure for further use. $^1$H NMR (CDCl$_3$): δ 7.72, 7.68, 7.51, 7.37, 7.20, 6.71, 4.85, 4.13, 3.91, 3.77, 3.62.

(S)-N-[[3-[3-Fluoro-4-(1H-indol-1-yl)phenyl]-2-oxo-5-oxazolidinyl]methyl]acetamide A solution of 336 mg (0.96 mmol) of the previous azide in 5 mL ethyl acetate was treated with 150 mg of 10% palladium on carbon followed by hydrogenation at one atomosphere for 18 h. The solution was filtered through celite, washing the filter cake with ethyl acetate. The filtrate was concentrated in vacuo to afford a light brown oil which was dissolved in 2 mL pyridine and treated with 0.2 mL acetic anhydride, followed by stirring at ambient temperature for 60 h. The solution was concentrated under high vacuum, and the residue was dissolved in chloroform and extracted with water. Drying (Na$_2$SO$_4$) and concentration in vacuo afforded a gum which was subjected to radial chromatography on a 4 mm chromatotron plate, eluting with 1.5% (v/v) methanol in dichloromethane and then with 2.5% (v/v) methanol in dichloromethane. These procedures afforded 277 mg (81%) of the title compound as a white solid. $^1$H NMR (CDCl$_3$): δ 7.70, 7.51, 7.33, 7.20, 6.71, 6.11, 4.84, 4.12, 3.87, 3.70, 2.06.

Example 6

(S)-N-[[3-[3-Fluoro-4-(1H-1,2,3-triazol-1-yl)phenyl]-2-oxo-5-oxazolidinyl]methyl]acetamide 3-Fluoro-1-nitro-4-(1H-1,2,3-triazol-1-yl)benzene A slurry of dibasic potassium phosphate, 38.0 g (0.218 mol), and 1H-1,2,3-triazole, 7.53 g (6.3 mL, 0.109 mol), in 325 mL dimethylsulfoxide was treated dropwise with 3,4-difluoronitrobenzene, 17.3 g (12.1 mL, 0.109 mol), with heating to 90° C. for 18 h. The mixture was cooled to room temperature, diluted with water (500 mL) and extracted with ethyl acetate (4×50 mL). Drying ($Na_2SO_4$) and concentrating in vacuo afforded a light yellow solid. This material was chromatographed over 600 g 230–400 mesh silica gel eluting with methylene chloride, 1% (v:v), 2% (v:v) and 5% (v:v) methanol-methylene chloride to afford 11.38 g (50%) of 3-Fluoro-1-nitro-4-(1H-1,2,3-triazol-1-yl)benzene as a light yellow solid, mp=123–124.5° C., along with 9.66 g (43%) of regioisomer 3-Fluoro-1-nitro-4-(2H-1,2,3-triazol-2-yl)benzene as a light yellow solid, mp 137–139° C.

3-Fluoro-1-(phenylmethoxycarbonylamino)-4-(1H-1,2,3-triazol-1-yl)benzene

A solution of 5.0 g (24.0 mmol) of the previous compound in 400 mL of 1:1 methanol-THF was treated with 3 g of W-2 Raney nickel. The mixture was hydrogenated on a Parr shaker under 45 psi hydrogen pressure for 18 h followed by filtering through celite, washing the filter cake with methanol. Concentration in vacuo afforded a white solid which was dissolved in 500 mL anhydrous THF, cooled to −20° C. and treated with sodium bicarbonate, 4.0 g (48.0 mmol) and benzyl chloroformate, 4.9 g (4.3 mL, 28.8 mmol). After stirring 72 h with gradual warming to room temperature, the solvent was removed under reduced pressure and the resulting oil was dissolved in 200 mL ethyl acetate. The mixture was extracted with water (3×50 mL), dried ($Na_2SO_4$) and concentrated in vacuo to give a yellow solid. This material was cchromatographed over 400 g 230–400 mesh silica gel eluting with methylene chloride, 1% (v:v) and 2% (v:v) methanol-methylene chloride to afford 6.18 g (82%) of the title compound as a white solid, mp 121–122° C.

(R)-[3-[3-Fluoro-4-(1H-1,2,3-triazol-1-yl)phenyl]-2-oxo-5-oxazolidinyl]methanol

A solution of 2.0 g (6.4 mmol) of the previous compound in 100 mL anhydrous THF at −78° C. was treated with 6.7 mL (1.0M, 6.7 mmol) of lithium bis(trimethylsilyl)amide in THF followed by stirring at −78° C. for 30 minutes. The mixture was treated with 960 mg (6.7 mmol) of R-(−)-glycidyl butyrate, followed by warming to 0° C. with gradual warming to room temperature. After 18 h, the mixture was quenched with saturated aqueous ammonium chloride (30 mL) and extracted with ethyl acetate (3×30 mL). Drying ($Na_2SO_4$) and concentration in vacuo gave a yellow oily solid. The crude material was recrystallized from boiling 2:1 methanol-ethyl acetate to afford 1.10 g (62%) of the title compound as a white solid, mp 179–180.5° C.

(R)-[3-[3-Fluoro-4-(1H-1,2,3-triazol-1-yl)phenyl]-2-oxo-5-oxazolidinyl]methylazide A slurry of 1.35 g (4.85 mmol) of the previous compound and 859 mg (1.18 mL, 8.49 mmol) triethylamine in 60 mL dichloromethane at 0° C. was treated with 695 mg (0.47 mL, 6.07 mmol) methanesulfonylchloride followed by warming to ambient temperature over 1 h. The mixture was then cooled to 0° C., treated with triethylamine, 859 mg (8.49 mmol), and methanesulfonyl chloride, 695 mg (6.07 mmol). After 5 minutes, the mixture was extracted with water (3×20 mL), saturated aqueous sodium bicarbonate (2×20 mL) and saturated aqueous sodium chloride (1×20 mL). Drying ($Na_2SO_4$) and concentration in vacuo afforded 1.89 g of the corresponding mesylate as a light yellow solid, which was dissolved in 90 mL DMF and treated with 4.73 g (72.8 mmol) sodium azide and warmed at 60° C for 18 h. The mixture was cooled to 0° C. and diluted with water (200 mL). The mixture was extracted with 1:1 ethyl ether-ethyl acetate (5×50 mL). The combined organic layers were then extracted with water (4×50 mL), dried ($Na_2SO_4$) and concentrated in vacuo to afford 1.48 g (ca. 100%) of the title azide as an off-white solid, sufficiently pure for further use. $^1$H NMR ($CDCl_3$) δ 8.09, 7.98, 7.87, 7.29, 4.86, 4.16, 3.94, 3.70.

(S)-N-[[3-[3-Fluoro-4-(1H-1,2,3-triazol-1-yl)phenyl]-2-oxo-5-oxazolidinyl]methyl]acetamide A solution of 300 mg (0.99 mmol) of the previous azide in 12 mL THF was treated with 750 mg of W-2 Raney nickel. The mixture was hydrogenated at atmospheric pressure for 18 h. The mixture was treated with 783 mg (0.80 mL, 9.9 mmol) pyridine, and 505 mg (0.47 mL, 4.9 mmol) acetic anhydride followed by stirring for 2 h. The mixture was filtered through celite, washing the filter cake with ethyl acetate. The filtrate was extracted with water (3×30 mL) and saturated aqueous sodium chloride (1×20 mL). Drying ($Na_2SO_4$) and concentration in vacuo gave an off-white solid. The crude material was recrystallized from boiling 10:1 ethyl acetate-hexane to give 210 mg (66%) of the title compound as a white solid, mp 193–194° C.

Example 7

(S)-N-[[3-[3-Fluoro-4-(1H-1,2,3-triazol-1-yl)phenyl]-2-oxo-5-oxazolidinyl]methyl]-2,2-dichloroacetamide A solution of 275 mg (0.91 mmol) of (R)-[3-[3-Fluoro-4-(1H-1,2,3-triazol-1-yl)phenyl]-2-oxo-5-oxazolidinyl]methylazide (from Example 6) in 15 mL THF was treated with 1.5 g of W-2 Raney nickel, and hydrogenated at atmospheric pressure. After 18 h, the mixture was filtered through celite, washing the filter cake with methanol. The filtrate was concentrated in vacuo and the resulting oil was slurried in 15 mL methylene chloride, cooled to 0° C. and treated with 138 mg (0.19 mL, 1.36 mmol) triethylamine, and 161 mg (0.11 mL, 1.09 mmol) dichloroacetyl chloride. After stirring at ambient temperature for 24 h, the mixture was diluted with methylene chloride and extracted with water (3×20 mL) and saturated aqueous sodium chloride (1×20 mL). Drying ($Na_2SO_4$) and concentration in vacuo afforded an off-white solid. The crude material was subjected to radial chromatography on a 4 mm chromatotron plate eluting with dichloromethane and 2% (v/v) methanol-dichloromethane. These procedures afforded 182 mg (52%) of the title compound as a white solid, mp 195–198° C. dec.

Example 8

(S)-N-[[3-[3-Fluoro-4-(2H-1,2,3-triazol-2-yl)phenyl]-2-oxo-5-oxazolidinyl]methyl]acetamide 3-Fluoro-1-(phenylmethoxycarbonylamino)-4-(2H-1,2,3-triazol-2-yl)benzene A solution of 6.0 g (28.82 mmol) of 3-fluoro-1-nitro-4-(2H-1,2,3-triazol-2-yl)benzene in 150 mL ethyl acetate and 25 mL methanol was treated with 750 mg of W-2 Raney Nickel. The mixture was hydrogenated on a Paar shaker under 45 psi hydrogen pressure for 24 h. The mixture was filtered through celite and the filtrate was concentrated in vacuo. The residue was dissolved in 150 mL acetone, treated with 72 mL saturated sodium bicarbonate solution, followed by cooling to 0° C. The mixture was treated with 6.15 g (5.14 mL, 36.08 mmol) of benzyl chloroformate, followed by stirring at 0° C. for 1 h, and then warming to ambient temperature for 3 h. The mixture was diluted with 500 mL water and 400 mL ethyl acetate. The aqueous phase was washed with 250 mL ethyl acetate and the combined organic layers were extracted with 300 mL saturated NaCl solution. Drying (Na$_2$SO$_4$) and concentration in vacuo afforded an amber oil which was recrystallized from hot chlorform-hexane to afford 7.52 g (84%) of the title compound as a white solid, mp 99.5–101° C.

(R)-[3-[3-Fluoro-4-(2H-1,2,3-triazol-2-yl)phenyl]-2-oxo-5-oxazolidinyl]methanol

A solution of 1.0 g (3.20 mmol) of the previous compound in 45 mL THF at −78° C. was treated with 3.52 mL (1.0M, 3.52 mmol) of lithium bis-(trimethylsilyl)amide in THF, followed by stirring at −78° C. for 30 min. The solution was treated with 508 mg (0.50 mL, 3.52 mmol) of (R)-(−)-glycidiyl butyrate followed by stirring at 0° C. for 30 min, and then to ambient temperature for 18 h. The mixture was diluted with 75 mL ethyl acetate and extracted with water (2×75 mL) and saturated NaCl solution (75 mL). Drying (Na$_2$SO$_4$) and concentration in vacuo afforded an amber oil, which was dissolved in 75 ml of methanol and treated with 1.0 g of K$_2$CO$_3$ followed by stirring for 2 h. The mixture was filtered and concentrated in vacuo to afford an amber oil which was chromatographed over 50 g of 230–400 mesh silica gel, eluting with 3% (v/v) methanol in dichloromethane. These procedures afforded 446 (50%) of the title compound as a white solid, mp 159–151° C.

(R)-[3-[3-Fluoro-4-(2H-1,2,3-triazol-2-yl)phenyl]-2-oxo-5-oxazolidinyl]methylazide A solution of 350 mg (1.26 mmol) of the previous alcohol and 2 mL of triethylamine in 8 mL dichloromethane at 0° C. was treated with 362 mg (1.64 mmol) of nosyl chloride, followed by stirring at 0° C. for 30 min, and warming to ambient temperature for 1 h. The mixture was diluted with 50 mL dichloromethane and was extracted with water (215.8 g×50 mL). Drying (Na$_2$SO$_4$) and concentration in vacuo afforded 540 mg (92%) of the corresponding nosylate, which was dissolved in 12 mL N,N-dimethylformamide and treated with 2 g of sodium azide, followed by stirring at ambient temperature for 48 h. The solution was dilutied with 125 mL ethyl acetate and extracted with water (5×50 mL). Drying (Na$_2$SO$_4$) and concentration in vacuo afforded a yellow solid, which was chromatographed over 50 g of 230–400 mesh silica gel, eluting with dichloromethane and then with 5% (v/v) acetone in dichloromethane. These procedures afforded 333 mg (94%) of the title azide as a faint yellow solid. $^1$H NMR (CDCl$_3$) δ 7.87, 7.70, 7.38, 4.84, 4.13, 3.91, 3.75, 3.63.

(S)-N-[[3-[3-Fluoro-4-(2H-1,2,3-triazol-2-yl)phenyl]-2-oxo-5-oxazolidinyl]methyl]acetamide A solution of the previous azide in 50 mL ethyl acetate was treated with 500 mg of W-2 Raney nickel followed by hydrogenation on a Paar shaker under 30 psi of hydrogen for 18 h. The mixture was filtered through celite, and the filtrated was concentrated in vacuo. The residue was dissolved in 8 mL pyridine and treated with 4 mL acetic anhydride followed by stirring at ambient temperature for 24 h. The solvents were removed under high vacuum (0.2 mm Hg) and the residue was dissolved in 75 mL ethyl acetate and extracted with water (2×50 mL) and saturated NaCl solution (50 mL). Drying (Na$_2$SO$_4$) and concentration in vacuo afforded an amber oil which was subjected to radial chromatography on a 4 mm chromatotron plate, eluting with 4% (v/v) methanol in dichloromethane. The material obtained was recrystallized from hot chloroform-hexane to afford 164 mg (47%) of the title compound. $^1$H NMR (CDCl$_3$) δ 7.87, 7.82, 7.70, 7.32, 6.21, 4.83, 4.10, 3.84, 3.68, 2.03.

Example 9

(S)-N-[[3-[3-Fluoro-4-(3-mercapto-4H-1,2,4-triazol-4-yl)phenyl]-2-oxo-5-oxazolidinyl]methyl]acetamide
4-(N-Benzylamino)-3-fluoronitrobenzene A solution of 23.9 g (16.9 mL, 0.15 mol) of 3,4-difluoronitrobenzene and 29.1 g (39.2 mL, 0.23 mol) of N,N-diisopropylethylamine in 285 mL acetonitrile was treated with 19.3 g (19.7 mL, 0.18 mol) of benzylamine, followed by warming at reflux for 5 h. The mixture was concentrated in vacuo and the residue was dissolved in 200 mL ethyl acetate, followed by extraction with water (3×50 mL). Drying (Na$_2$SO$_4$) and concentration in vacuo afforded a yellow solid, which was recrystallized from hot ethyl acetate-hexane to afford 32.25 g (87%) of the title compound as yellow-orange needles, mp 97.5–99° C.

4-(N-Benzylbenzyloxycarbonylamino)-1-(benzyloxycarbonylamino)-3-fluorobenzene

A solution of 14.25 g (0.058 mol) of the previous compound in 800 mL THF was treated with 1.0 g of 5% platinum on carbon, followed by hydrogenation on a Parr shaker under 30 psi hydrogen pressure for 18 h. The mixture was filtered through celite, washing the filter cake with ethyl acetate. The filtrate was concentrated in vacuo to afford an oily residue which was dissolved in 1.0 L of THF and treated with 15.8 g (16.5 mL, 0.13 mol) of N, N-dimethylaniline. The solution was cooled to 0° C. and 21.72 g (18.18 mL, 0.127 mol) of benzyl chloroformate was added dropwise over 3 min. The solution was stirred at 0° C. for 30 min and then was allowed to gradually warm to ambient temperature, followed by stirring for 23 h. The solution was concentrated in vacuo and the residue was dissolved in 1 L of ethyl acetate. The mixture was washed with 80 mL cold 1N HCl solution, 80 mL water, and 80 mL saturated NaHCO$_3$ solution. The solution was dried (MgSO$_4$) and concentrated in vacuo to afford an oil which was chromatographed over 500 g of 230–400 mesh silica gel, eluting with 10–15% (v/v) ethyl acetate in hexane. These procedures afforded 12.42 g (44%) of the title compound as a white solid, mp 101–102.5° C.

(R)-[3-[3-Fluoro-4-(N-benzylbenzyloxycarbonylamino)phenyl]-2-oxo-5-oxazolidinyl]methanol A solution of 12.42 g (0.026 mol) of the previous compound in 375 mL THF at −78° C. was treated with 16.7 mL (1.6M, 0.027 mol) of n-butyllithium in hexanes dropwise over 6 min, followed by stirring at −78° C. for 30 min. The solution was then treated with 4.6 g (4.5 mL, 0.032 mol) of (R)-(−)-glycidyl butyrate, followed by stirring at −78° C. for 1 h, and warming to ambient temperature for 20 h. The solution was treated with 25 mL saturated ammonium chloride solution, followed by addition of 25 mL water and 300 mL ethyl acetate. The aqueous phase was extracted with ethyl acetate and the combined organic layers were dried (MgSO$_4$) and concentrated in vacuo. The oil obtained was chromatographed over 400 g of 230–400 mesh silica gel, eluting with 1% (v/v) methanol in dichloromethane. These procedures afforded 7.56 g (66%) of the title compound as a white solid. $^1$H NMR (CDCl$_3$) δ 7.48, 7.25, 7.07, 6.95, 5.15, 4.18, 4.67, 3.91, 3.69.

(S)-N-[3-[3-Fluoro-4-(N-benzylbenzyloxycarbonylamino)phenyl]-2-oxo-5-oxazolidinyl]methylacetamide A solution of 8.23 g (18.3 mmol) of the prevous compound and 3.24 g (4.5 mL, 32.0 mmol) of triethylamine in 107 mL dichloromethane at 0° C. was treated with 5.47 g of nosyl chloride, followed by stirring at 0° C. for 4 h. The mixture was diluted with dichloromethane and extracted with water (2×). Drying (Na$_2$SO$_4$) and concentration in vacuo afforded a yellow foam, which was dissolved in 58 ml isopropyl alcohol, 93 mL acetonitrile, and 116 mL ammonium hydroxide, followed by warming at 40° C. for 18 h. The mixture was cooled, diluted with ethyl acetate and extracted with water (3x) and saturated NaCl solution. Drying ($Na_2SO_4$) and concentration in vacuo afforded a yellow foam, which was dissolved in 200 ml of ethyl acetate and treated with 4.67 g (4.3 mL, 45.75 mmol) of pyridine and 7.24 g (7.4 mL, 91.5 mmol) of acetic anhydride. The solution was stirred at ambient temperature for 18 h, followed by extraction with water (3x) and saturated NaCl solution. Drying ($Na_2SO_4$) and concentration in vacuo afforded an amber foam, which was chromatographed over 450 g of 230–400 mesh silica gel, eluting with 1% (v/v) methanol in dichloromethane. These procedures afforded 7.04 g (78%) of the title compound as a light yellow rigid foam. High Resolution Mass Spectrum (EI): calcd for $C_{27}H_{26}FN_3O_5$: 491.1856. found: 491.1860.

(S)-N-[3-[3-Fluoro-4-aminophenyl]-2-oxo-5-oxazolidinyl]methylacetamide

A solution of 5.6 g (11.4 mmol) of the previous compound in 200 mL ethanol was treated with 200 mg of 10% palladium on carbon, followed by hydrogenation on a Parr shaker under 45 psi of hydrogen pressure for 24 h. The mixture was filtered through celite, washing the filter cake with methanol. The filtrate was concentrated in vacuo to afford an off-white solid, which was recrystallized from hot ethyl acetate-hexane to afford 2.81 g (92%) of the title compound as an off-white solid. $^1$H NMR (DMSO) δ 8.20, 7.29, 6.95, 6.76, 5.00, 4.65, 4.00, 3.63, 3.37, 1.83.

(S)-N-[3-[3-Fluoro-4-isothiocyanophenyl]-2-oxo-5-oxazolidinyl]methylacetamide

A solution of 960 mg (4.12 mmol) of 1,1'-thiocarbonyldi-2(1H)-pyridone in 30 mL dichloromethane at 0° C. was treated with 1.0 g (3.74 mmol) of the previous compound in one portion. The mixture was stirred at 0° C. for 2.5 h, followed by warming to ambient temperature for 2 h. The mixture was concentrated in vacuo and the solid obtained was triturated with 15 mL water. The product was collected by filtration and washed with a small amount of water, followed by drying overnight in a vacuum oven. These procedures afforded 1.09 g (94%) of the title compound as a white solid, mp 172.5–176° C.

(S)-N-[3-[3-Fluoro-4-[3-mercapto-4H-1,2,4-triazol-4-yl] phenyl]-2-oxo-5-oxazolidinyl]methylacetamide A solution of 1.11 g (3.59 mmol) of the previous compound in 26 mL THF was treated with 230 mg (3.77 mmol) of formic hydrazide followed by warming at 70° C. for 3.5 h. The mixture was cooled, and the precipitate was collected by filtration and washed with ethyl acetate. The solid was dried in a vacuum oven at 60° C. to afford 1.2 g of a solid. Of this material, 100 mg (0.27 mmol) was suspended in 2 mL water and treated with 0.28 mL (0.97M, 0.27 mmol) of KOH solution, followed by stirring for 45 min. The solution was then treated with 0.28 mL (1.0N, 0.28 mmol) of HCl solution. The precipitate was collected by filtration and washed with a small amount of 1N HCl solution. The solid was dried in a vacuum oven at ambient temperature. These procedures afforded 83 mg of the title compound as a white solid, mp 269–271° C.

Example 10

(S)-N-[[3-[3-Fluoro-4-(3-methylthio-4H-1,2,4-triazol-4-yl)phenyl]-2-oxo-5-oxazolidinyl]methyl]acetamide A suspension of 200 mg (0.57 mmol) of the compound of Example 9 and 121 mg (53 μL, 0.85 mmol) of methyl iodide in 5 mL methanol was treated with 53 mg (0.63 mmol) of solid sodium bicarbonate. The mixture was stirred at ambient temperature for 23 h, and the precipitated solid was collected by filtration, and the filter cake was washed with methanol. The filtrate was concentrated in vacuo to afford a gum which was chromatographed over 25 g of 230–400 mesh silica gel, eluting with 5% (v/v) methanol and 0.5% (v/v) ammonium hydroxide in dichloromethane. These procedures afforded a white solid, which was recrystallized from methanol to afford 128 mg (61%) of the title compound as a white solid, mp 188.5–190.5° C.

Example 11

(S)-N-[[3-[3-Fluoro-4-(4H-1,2,4-triazol-4-yl)phenyl]-2-oxo-5-oxazolidinyl]methyl]acetamide 330 mg (0.938 mmol) of the mercaptan of Example 9 was added to 0.6 mL of 20% nitric acid solution, followed by warming on a steam bath for ca. 1 min. After this time, an additional 0.6 mL of 20% nitric acid was added, followed by warming on a steam bath for 6–7 min, at which point all solids had gone into solution. The mixture was cooled to 0° C. and adjusted to pH9 by addition of ammonium hydroxide solution. The mixture was concentrated in vacuo to afford a brown gummy oil, which was chromatographed over 25 g of 230–400 mesh silica gel, eluting with 5% (v/v) methanol and 0.5% (v/v) ammonium hydroxide in dichloromethane to afford a solid, which was recrystallized from acetonitrile to afford the title compound, mp 204.5–206° C.

Example 12

(S)-N-[[3-[3-Fluoro-4-(1H-pyrrol-1-yl-3-carboxaldehyde)phenyl]-2-oxo-5-oxazolidinyl]methyl] acetamide A solution of 2.0 g (7.5 mmol) of the aniline derivative of Example 9 and 1.68 g (10.5 mmol) of 2,5-dimethoxy-3-tetrahydrofurancarboxaldehyde in 55 mL glacial acetic acid was warmed at reflux for 2 h. The solution was cooled and the solvent removed under high vacuum, azeotroping the residue with toluene to remove the last traces of acetic acid. The residue was chromatographed over 300 g of 230–400 mesh silica gel, eluting with dichloromethane and then with 1–3% (v/v) methanol in dichloromethane. These procedures afforded 2.21 g of the title compound as a light yellow amorphous solid. Resolution Mass Spectrum: calcd for $C_{17}H_{16}FN_3O_4$: 345.1125. found: 345.1129.

Example 13

(S)-N-[[3-[3-Fluoro-4-(3-hydroxymethyl-1H-pyrrol-1-yl) phenyl]-2-oxo-5-oxazolidinyl]methyl]acetamide A solution of 125 mg (0.36 mmol) of the previous compound in 4 mL methanol and 2 mL dichloromethane at 0° C. was treated with 7 mg (0.18 mmol) of sodium borohydride. The solution was allowed to warm to ambient temperature for 4 h, followed by dilution with 30 mL dichloromethane and extraction with water. Drying ($Na_2SO_4$) and concentration in vacuo afforded a white solid, which was recrystallized from ethyl acetate-methanol-hexane. These procedures afforded 106 mg (84%) of the title compound as a white solid. High Resolution Mass Spectrum (EI): calcd for $C_{17}H_{18}FN_3O_4$: 347.1281. found: 347.1274.

Example 14

(S)-N-[[3-[3-Fluoro-4-(3-carbomethoxy-1H-pyrrol-1-yl) phenyl]-2-oxo-5-oxazolidinyl]methyl]acetamide A solution of 220 mg (0.64 mmol) of the compound of Example 12 in 10 mL of 1:1 acetonitrile-methanol was treated with 164 mg (0.64 mmol) of sodium cyanide, 1.15 g (13.2 mmol) of activated manganese dioxide, and 60 mg (58 μL, 1.0 mmol) of glacial acetic acid. The mixture was stirred at ambient temperature for 36 h, at which point 550 mg (6.32 mmol) of activated manganese dioxide and 60 mg (58 μL, 1.0 mmol) of glatial acetic acid were added. The solution was stirred for an additional 24 h, and was filtered through celite, washing the filter cake with methanol. The filtrate was concentrated in vacuo, diluted with ethyl acetate and extracted with water (3×). The organic layer was dried ($Na_2SO_4$) and concentrated in vacuo to afford a pink solid. This material was subjected to radial chromatography on a 2 mm chromatotron plate, eluting with dichloromethane and then with 1–2% (v/v) methanol in dichloromethane. These procedures afforded 170 mg (71%) of the title compound as a white solid. Analysis: calcd for $C_{18}H_{18}FN_3O_5$: C, 57.60; H, 4.83; N, 11.20. found: C, 57.29; H, 5.19; N, 11.07.

Example 15

(S)-N-[[3-[3-Fluoro-4-(1H-pyrrol-1-yl-3-carboxaldehyde)phenyl]-2-oxo-5-oxazolidinyl]methyl] acetamide, methoxime A solution of 150 mg (0.43 mmol) of the compound of Example 12 in 5 mL of 1:1 methanol-dichloromethane was treated with 44 mg (0.52 mmol) of methoxylamine hydrochloride and 36 mg (0.26 mmol) of potassium carbonate, followed by stirring at ambient temperature for 18 h. The mixture was diluted with dichloromethane and was extracted with water (3×). Drying ($Na_2SO_4$) and concentration in vacuo afforded a red-brown-solid. This material was subjected to radial chromatography on a 2 mm chromatotron plate, eluting with dichloromethane and then with 1–2% (v/v) methanol in dichloromethane. These procedures afforded 101 mg (63%) of the title compound as a white solid which was a mixture of E- and Z- double bond stereoisomers. High Resolution Mass Spectrum (EI): calcd for $C_{18}H_{19}FN_4O_4$: 374.1390. found: 374.1390.

Example 16

(S)-N-[[3-[3-Fluoro-4-(3-(hydroxyiminomethyl)-1H-pyrrol-1-yl)phenyl]-2-oxo-5-oxazolidinyl]methyl] acetamide A solution of 150 mg (0.43 mmol) of the aldehyde of Example 12 and 36 mg (0.26 mmol) of potassium carbonate in 10 mL of 1:1 methanol-dichloromethane was treated with 36 mg (0.52 mmol) of hydroxylamine hydrochloride, followed by stirring at ambient temperature for 48 h. The mixture was diluted with ethyl acetate, extracted with water (3×), dried ($Na_2SO_4$) and concentrated in vacuo to afford an off-white solid. This material was subjected to radial chromatography on a 2 mm chromatotron plate, eluting with 2–4% (v/v) methanol in dichloromethane. These procedures afforded 90 mg (58%) of the title compound as a white solid. $^1$H NMR (DMSO) δ 11.07, 10.5, 8.24, 8.01, 7.85, 7.70, 7.62, 7.40, 7.30, 7.14, 6.63, 6.48, 4.75, 4.16, 3.77, 3.42, 1.83.

Example 17

(S)-N-[[3-[3-Fluoro-4-(4-acetyl-1H-1,2,3-triazol-1-yl) phenyl]-2-oxo-5-oxazolidinyl]methyl]acetamide
(S)-N-[[3-[4-Azido-3-fluorophenyl]-2-oxo-5-oxazolidinyl] methyl]acetamide A solution of 4.0 g (14.96 mmol) of (S)-N-[3-[3-Fluoro-4-aminophenyl]-2-oxo-5-oxazolidinyl]methylacetamide from Example 9 in 40 mL of 6N HCl solution at 0° C. was treated portionwise with 4.12 g (59.84 mmol) of sodium nitrite, followed by stirring at 0° C. for 2 h. The mixture was then treated in several portions with a solution of 1.94 g (29.92 mmol) of sodium azide and 24.52 g (0.30 mol) of sodium acetate in in 50 mL of water. After addition was complete, solution was extracted with ethyl acetate, and the organic layer was dried ($Na_2SO_4$) and concentrated in vacuo to afford 4.1 g (93%) of the title compound as a light yellow solid, sufficiently pure for further use. $^1$H NMR ($CDCl_3$) δ 8.22, 7.59, 7.33, 4.72, 4.10, 3.72, 3.40, 1.90.

(S)-N-[[3-[3-Fluoro-4-(4-acetyl-1H-1,2,3-triazol-1-yl) phenyl]-2-oxo-5-oxazoldinyl]methyl]acetamide A solution of 500 mg (1.7 mmol) of the previous azide in 25 ml benzene was treated with 347 mg (5.1 mmol) of 3-butyn-2-one followed by warming at reflux for 18 h. The mixture was cooled and the 407 mg (66%) of the title compound was isolated by filtration of the reaction mixture. High Resolution Mass Spectrum (EI): calcd for $C_{16}H_{16}FN_5O_4$: 361.1186. found: 361.1183.

Example 18

(S)-N-[[3-[3-Fluoro-4-(4-(1-hydroxyethyl)-1H-1,2,3-triazol-1-yl)phenyl]-2-oxo-5-oxazolidinyl]methyl] acetamide A solution of 150 mg (0.40 mmol) of the compound of Example 17 in 10 mL 1:1 THF-methanol was treated with 15 mg (0.4 mmol) of sodium borohydride followed by stirring at ambient temperature for 18 h. The mixture was concentrated in vacuo, dissolved in 1:1 methanol-dichloromethane and filtered. The filtrate was concentrated in vacuo and the residue was subjected to radial chromatography on a 2 mm chromatotron plate. These procedures afforded 120 mg (80%) of the title compound as a white solid. Mass Spectrum (EI): m/z 363, 291, 276, 232, 217, 207, 191, 179, 163, 148, 135, 123, 85, 56.

Example 19

(S)-N-[[3-[3-Fluoro-4-(4-(1-hydroxyiminomethyl)-1H-1, 2,3-triazol-1-yl)phenyl]-2-oxo-5-oxazolidinyl]methyl] acetamide A solution of 150 mg (0.40 mmol) of the compound of Example 17 in 10 mL of 1:1 THF-methanol was treated with 66 mg (0.96 mmol) of hydroxylamine hydrochloride and 66 mg (0.48 mmol) of potassium carbonate, followed by stirring at ambient temperature for 8 h, and then warming at reflux for 2 h. The mixture was concentrated in vacuo, and the residue was subjected to radial chromatography on a 2 mm chromatotron plate, eluting with 5% (v/v) methanol in dichloromethane. These procedures afforded 30 mg (20%) of the title compound as a white solid. MassSpectrum (EI): m/z 376, 332, 318, 287, 274, 245, 220, 202, 187, 175, 163, 149, 139, 82, 56.

Example 20

(S)-N-[[3-[3-Fluoro-4-(4-carbomethoxy-1H-1,2,3-triazol-1-yl)phenyl]-2-oxo-5-oxazolidinyl]methyl] acetamide A solution 1.0 g (3.4 mmol) of the azide of Example 17 in 50 mL benzene was treated with 573 mg (6.8 mmol) of methyl propiolate followed by warming at reflux for 24 h. The mixture was cooled and the product isolated by filtration of the reaction mixture. These procedures afforded 880 mg of the title compound as a white solid. High Resolution Mass Spectrum (EI): calcd for $C_{16}H_{16}FN_5O_5$: 377.1135. found: 377.1131.

Example 21

(S)-N-[[3-[3-Fluoro-4-(1H-1,2,3-triazol-1-yl-4-carboxaldehyde)phenyl]-2-oxo-5-oxazolidinyl]methyl] acetamide A solution of 1.70 g (5.8 mmol) of the azide of example 17 in 50 mL benzene was treated with 4.46 g (34.8 mmol) of 1,1-diethoxy-2-propyne followed by warming at reflux for 18 h. The solution was treated with 1.0 g (7.80 mmol) of 1,1-diethoxy-2-propyne followed by warming at reflux for an additional 3 h. The solution was cooled and concentrated in vacuo to afford an oil which was chromatographed over 200 g of 230–400 mesh silica gel, eluting with 2–3% (v/v) methanol in dichloromethane to afford 2.0 g (80%) of (S)-N-[[3-[3-Fluoro-4-(4-(diethoxymethyl)-1H-1,2,3-triazol-1-yl)phenyl]-2-oxo-5-oxazoldinyl]methyl]acetamide and (S)-N-[[3-[3-Fluoro-4-(5-(diethoxymethyl)-1H-1,2,3-triazol-1-yl)phenyl]-2-oxo-5-oxazoldinyl]methyl]acetamide as an inseparable mixture of isomers. Of this material, 410 mg (0.973 mmol) was dissolved in 10 mL THF and treated with 1 mL of 1N HCl solution followed by stirring at ambient temperature for 48 h, and then warming at reflux for 1 h. The mixture was dissolved in ethyl acetate and extracted with water. Drying ($Na_2SO_4$) and concentration in vacuo afforded an oil which was subjected to radial chromatography on a 2 mm chromatotron plate eluting with 7% (v/v) methanol in dichloromethane. The less polar fraction [110 mg (33%)] from the chromatography proved to be the title compound, isolated as a white solid. $^1$H NMR ($CDCl_3$) δ 8.60, 7.99, 7.85, 7.36, 6.1, 4.86, 4.12, 3.89, 3.72, 2.04.

Example 22

(S)-N-[[3-[3-Fluoro-4-(4-hydroxymethyl-1H-pyrazol-1-yl)phenyl]-2-oxo-5-oxazolidinyl]methyl]acetamide
Methyl 3-pyrazolecarboxylate hydrochloride 10 mL of methanol at 0° C. was treated dropwise with 1 mL acetyl chloride, followed by addition of 2.0 g (17.84 mmol) of 4-pyrazolecarboxylic acid, followed by warming the mixture at reflux for 18 h. The solution was cooled and concentrated in vacuo to afford 2.6 g (90%) of the title compound as a white solid. $^1$H NMR ($CD_3OD$) δ 8.25, 3.86.

4-(4-Carbomethoxy-1H-pyrazol-1-yl)-3-Fluoro-1-nitrobenzene

A solution of 2.9 g (17.84 mmol) of the previous compound and 4.93 g (35.68 mmol) of potassium carbonate in 85 mL DMSO was treated with 2.83 g (17.84 mmol) of 3,4-difluoronitrobenzene. The solution was warmed at 90° C. for 16 h, followed by cooling, dilution with chloroform and extraction with water (5×). Drying ($Na_2SO_4$) and concentration in vacuo afforded 4.17 g (88%) of the title compound as an off-white solid. $^1$H NMR ($CDCl_3$) δ 8.65, 8.28, 8.20, 3.91.

4-(4-Carbomethoxy-1H-pyrazol-1-yl)-3-Fluoro-1-(phenylmethoxycarbonylamino)benzene A solution of 4.17 g (15.7 mmol) of the previous compound in 200 mL THF was treated with 1 g of W-2 Raney nickel, followed by hydrogenation on a Parr shaker under 45 psi hydrogen pressure for 18 h. The mixture was filtered through celite, and the filtrate concentrated in vacuo to afford an off-white solid, which was dissolved in 30 mL THF and 5 mL acetone and treated with 34 mL saturated sodium bicarbonate solution, followed by cooling to 0° C. and and addition of 3.21 g (2.69 mL, 18.8 mmol) of benzyl chloroformate. The solution was stirred at 0° C. for 1 h, and then was allowed to warm to ambient temperature for 18 h. The mixture was concentrated in vacuo, and the resulting aqueous layer was extracted with ethyl acetate (3×). The organic layer was dried ($Na_2SO_4$) and concentrated in vacuo to afford 3.1 g (53%) of the title compound as a white solid. $^1$H NMR ($CDCl_3$) δ 8.41, 8.10, 7.79, 7.64, 7.40, 7.10, 6.88, 5.23, 3.88.

4-(4-hydroxymethyl-1H-pyrazol-1-yl)-3-Fluoro-1-(phenylmethoxycarbonylamino)benzene A solution of 3.0 g (8.13 mmol) of the previous compound in 20 mL anhydrous THF was treated with 1.42 g (65.04 mmmol) of lithium borohydride, followed by stirring at ambient temperature for 18 h. The solution was treated with 5 mL saturated sodium bicarbonate solution, followed by concentration in vacuo. The mixture was diluted with ethyl acetate and extracted with water. Drying ($Na_2SO_4$) and concentration in vacuo afforded a residue which was chromatographed over 150 g of 230–400 mesh silica gel, eluting with 2% (v/v) methanol in dichloromethane. These procedures afforded 1.63 g (59%) of the title compound as a white solid. High Resolution Mass Spectrum (EI): calcd for $C_{18}H_{16}FN_3O_3$: 341.1176. found: 341.1180.

4-(4-[(tetrahydropyran-2-yl)oxymethyl]-1H-pyrazol-1-yl)-3-Fluoro-1-(phenylmethoxycarbonylamino)benzene A solution of 1.63 g (4.77 mmol) of the previous compound in 30 mL dichloromethane was treated with 400 mg (4.75 mmol) of dihydropyran and 10 mg of p-toluenesulfonic acid. The solution was stirred at ambient temperature for 18 h, followed by extraction with 30 mL saturated sodium bicarbonate solution and water (30 mL). Drying ($Na_2SO_4$) and concentration in vacuo afforded a solid which was chromatographed over 85 g of 230–400 mesh silica gel eluting with 20% (v/v) ethyl acetate in hexane. These procedures afforded 2.0 g (99%) of the title compound as a white solid. High Resolution Mass Spectrum (EI): calcd for $C_{23}H_{24}FN_3O_4$: 425.1751. found: 425.1747.

(R)-[3-[3-Fluoro-4-(4-[(tetrahydropyran-2-yl)oxymethyl]-1H-pyrazol-1-yl)phenyl]-2-oxo-5-oxazolidinyl]methanol A solution of 1.43 g (3.36 mmol) of the previous compound in 10 mL THF at −78° C. was treated with 3.7 mL (1.0M, 3.7 mmol) of lithium bis(trimethylsilyl)amide in THF, followed by stirring at 78° C. for 30 min. The solution was then treated with 533 mg (0.52 mL, 3.7 mmol) of (R)-(–)-glycidyl butyrate followed by stirring at 78° C. for 30 min, warming to 0° C. for 30 min, and then gradual warming to ambient temperature for 18 h. The solution was treated with 1 mL saturated ammonium chloride solution and diluted with ethyl acetate. The mixture was extracted with with water, dried ($Na_2SO_4$) and concentrated in vacuo. The residue was chromatographed over 70 g of 230–400 mesh silica gel, eluting with 2% (v/v) methanol in dichloromethane. These procedures afforded 910 mg (70%) of the title compound as a white solid. High resolution Mass Spectrum (EI): calcd for $C_{19}H_{22}FN_3O_5$: 391.1543. found: 391.1542.

(R)-[3-[3-Fluoro-4-(4-[(tetrahydropyran-2-yl)oxymethyl]-1H-pyrazol-1-yl)phenyl]-2-oxo-5-oxazolidinyl]methanesulfonyloxymethane A solution 0.820 mg (2.1 mmol) of the previous compound and 318 mg (3.15 mmol) triethylamine in 25 mL of dichloromethane at 0° C. was treated with 360 mg (2.62 mmol) of methanesulfonyl chloride. The solution was stirred at 0° C. for 1 h. The solution was diluted with dichloromethane and extracted with water. Drying ($Na_2SO_4$) and concentration in vacuo afforded 986 mg (99%) of the title compound as a white solid. $^1$H NMR ($CDCl_3$) δ 7.95, 7.92, 7.74, 7.25, 4.97, 4.75, 4.50, 4.20, 4.01, 3.93, 3.59, 3.12, 1.85, 1.74, 1.56.

(R)-[3-[3-Fluoro-4-(4-[(tetrahydropyran-2-yl)oxymethyl]-1H-pyrazol-1-yl)phenyl]-2-oxo-5-oxazolidinyl]methyl azide A solution of 986 mg (2.1 mmol) of the previous compound and 683 mg (10.5 mmol) of sodium azide in 20 mL DMF was warmed at 60° C. for 18 h, followed by dilution with ethyl acetate and extraction with water. Drying (Na$_2$SO$_4$) and concentration in vacuo afforded 874 mg (99%) of the title compound as a white solid. $^1$H NMR (CDCl$_3$) δ 7.98, 7.87, 7.74, 7.23, 4.82, 4.72, 4.50, 4.11, 3.90, 3.73, 3.61, 3.55, 1.81, 1.73, 1.58.

(S)-N-[[3-[3-Fluoro-4-(4-[(tetrahydropyran-2-yl)oxymethyl]-1H-pyrazol-1-yl)phenyl]-2-oxo-5-oxazolidinyl]methyl]acetamide A solution of 874 mg (2.1 mmol) of the previous compound in 15 mL ethyl acetate was treated 200 mg of 10% palladium on carbon, followed by hydrogenation at one atmosphere for 1.5 h. The solution was filtered through celite and the filtrate concentrated in vacuo to afford a brown solid, which was dissolved in 3 mL pyridine and treated with 428 mg (4.2 mmol) of acetic anhydride, followed by stirring at ambient temperature for 18 h. The solution was diluted with ethyl acetate and extracted with water. Drying (Na$_2$SO$_4$) and concentration in vacuo afforded a solid which was chromatographed over 50 g of 230–400 mesh silica gel eluting with 1–2% (v/v) methanol in dichloromethane. These procedures afforded 626 mg (69%) of the title compound as a white solid. High Resolution Mass Spectrum (EI): calcd for C$_{21}$H$_{25}$FN$_4$O$_5$: 432.1809. found: 432.1811.

(S)-N-[[3-[3-Fluoro-4-(4-hydroxymethyl-1H-pyrazol-1-yl)phenyl]-2-oxo-5-oxazolidinyl]methyl]acetamide A solution of 300 mg (0.693 mmol) of the previous compound in 15 mL methanol was treated with 40 mg of p-toluenesulfonic acid, followed by stirring at ambient temperature for 18 h. The mixture was concentrated in vacuo and the residue dissolved in ethyl acetate and extracted with saturated sodium bicarbonate solution and water. Drying (Na$_2$SO$_4$) and concentration in vacuo afforded 140 mg (58%) of the title compound as a white solid. High Resolution Mass Spectrum (EI): calcd for C$_{16}$H$_{17}$FN$_4$O$_4$: 349.1312. found: 349.1321.

Example 23

(S)-N-[[3-[3-Fluoro-4-[3-(2-carboethoxyvinyl)-1H-pyrrol-1-yl]phenyl]-2-oxo-5-oxazolidinyl]methyl]acetamide A solution of 805 mg (3.19 mmol) of diisopropyl ethoxycarbonylmethylphosphonate in 7 mL THF at 0° C. was treated with 3.19 mL (1.0M, 3.19 mmol) of potassium tert-butoxide in THF solution, followed by warming to ambient temperature for 1 h. The solution was cooled to −78° C. and treated via cannula with a solution of 500 mg (1.45 mmol) of the compound of Example 12 in 4 mL THF. The solution was stirred at −78° C. for 30 min, followed by warming to ambient temperature for 2 h. The solution was quenched by addition of 1 mL saturated ammonium chloride solution followed by dilution with ethyl acetate and extraction with water. Drying (Na$_2$SO$_4$) and concentration in vacuo afforded a yellow solid, which was chromatographed over 100 g of 230–400 mesh silica gel, eluting with 1–2% (v/v) methanol in dichloromethane. These procedures afforded 497 mg (83%) of the title compound as a light yellow solid. $^1$H NMR (CDCl$_3$) δ 7.65, 7.37, 7.27, 7.20, 6.97, 6.56, 6.17, 6.02, 4.82, 4.24, 4.08, 3.83, 3.70, 2.04, 1.33.

Example 24

(S)-N-[[3-[3-Fluoro-4-[3-(2-carboethoxyethyl)-1H-pyrrol-1-yl]phenyl]-2-oxo-5-oxazolidinyl]methyl]acetamide A solution of 150 mg (0.36 mmol) of the compound of Example 23 and 54 mg (0.54 mmol) of copper [I] chloride in 15 mL 1:1 Methanol-THF at 0° C. was treated with 136 mg (3.6 mmol) of sodium borohydride. The solution was stirred at 0° C. for 30 min and then warmed to ambient temperature for 1 h. The solution was treated with 2 mL saturated ammonium chloride solution, followed by filtration through celite. The filtrate was concentrated in vacuo and the residue was diluted with ethyl acetate and extracted with water (3×). Drying (Na$_2$SO$_4$) and concentration in vacuo afforded 150 mg (99%) of the title compound as a white solid. $^1$H NMR (CDCl$_3$) δ 7.60, 7.34, 7.33, 6.91, 6.81, 6.21, 5.97, 4.81, 4.15, 4.08, 3.82, 3.72, 3.65, 2.87, 2.62, 2.04, 1.26.

Example 25

(S)-N-[[3-[3-Fluoro-4-[3-(3-hydroxypropyl)-1H-pyrrol-1-yl]phenyl]-2-oxo-5-oxazolidinyl]methyl]acetamide A solution of 275 mg (0.66 mmol) of the compound of Example 24 in 15 mL THF was treated with 287 mg (13.2 mmol) of lithium borohydride followed by stirring at ambient temperature for 18 h. The solution was treated with 1 mL of saturated ammonium chloride solution, diluted with ethyl acetate, and extracted with water (3×). Drying (Na$_2$SO$_4$) and concentration in vacuo afforded an oil, which was chromatographed over 20 g of 230–400 mesh silica gel eluting with 2–4% (v/v) methanol in dichloromethane. These procedures afforded 96 mg (39%) of the title compound as a white solid. $^1$H NMR (CDCl$_3$) δ 7.74, 7.66, 7.38, 7.27, 7.18, 6.95, 6.61, 5.98, 4.82, 4.37, 4.27, 4.09, 3.83, 3.68, 2.88, 2.82, 2.62, 2.04, 1.79.

Example 26

(S)-N-[[3-[3-Fluoro-4-[3-(3-methanesulfonylaminopropyl)-1H-pyrrol-1-yl]phenyl]-2-oxo-5-oxazolidinyl]methyl]acetamide A solution of 100 mg (0.266 mmol) of the compound of Example 25 (previously dried at 60° C. under 0.1 mmHg for 18 h prior to use) and 88 mg (120 μL, 0.88 mmol) of triethylamine in 2 mL dichloromethane at 0° C. was treated with 85 mg (58 μL, 0.73 mmol) of methanesulfonyl chloride, followed by stirring at 0° C. for 30 min. The solution was diluted with dichloromethane and extracted with water (2×) and saturated sodium bicarbonate solution. Drying (Na$_2$SO$_4$) and concentration in vacuo afforded a solid which was dissolved in 2 mL DMF and treated via cannula to a 0° C. solution of 38 mg (0.40 mmol) of methanesulfonamide in 2 mL DMF which had been previously treated with 10 mg (17 mg of 60% in oil, 0.43 mmol) of sodium hydride. The solution was then warmed at 60° C. for 18 h. The solution was cooled and the DMF removed in vacuo, and the residue was dissolved in ethyl acetate and extracted with water (2×). Drying (Na$_2$SO$_4$) and concentration in vacuo afforded a solid which was subjected to radial chromatography on a 2 mm chromatotron plate, eluting with 1–4% (v/v) methanol in dichloromethane. These procedures afforded 31 mg (26%) of the title compound as a white solid. $^1$H NMR (CDCl$_3$) δ 7.61, 7.56, 7.35, 7.23, 6.92, 6.81, 6.19, 6.06, 4.81, 4.29, 4.07, 3.82, 3.67, 3.22, 2.95, 2.62, 2.04, 1.90.

CHART I
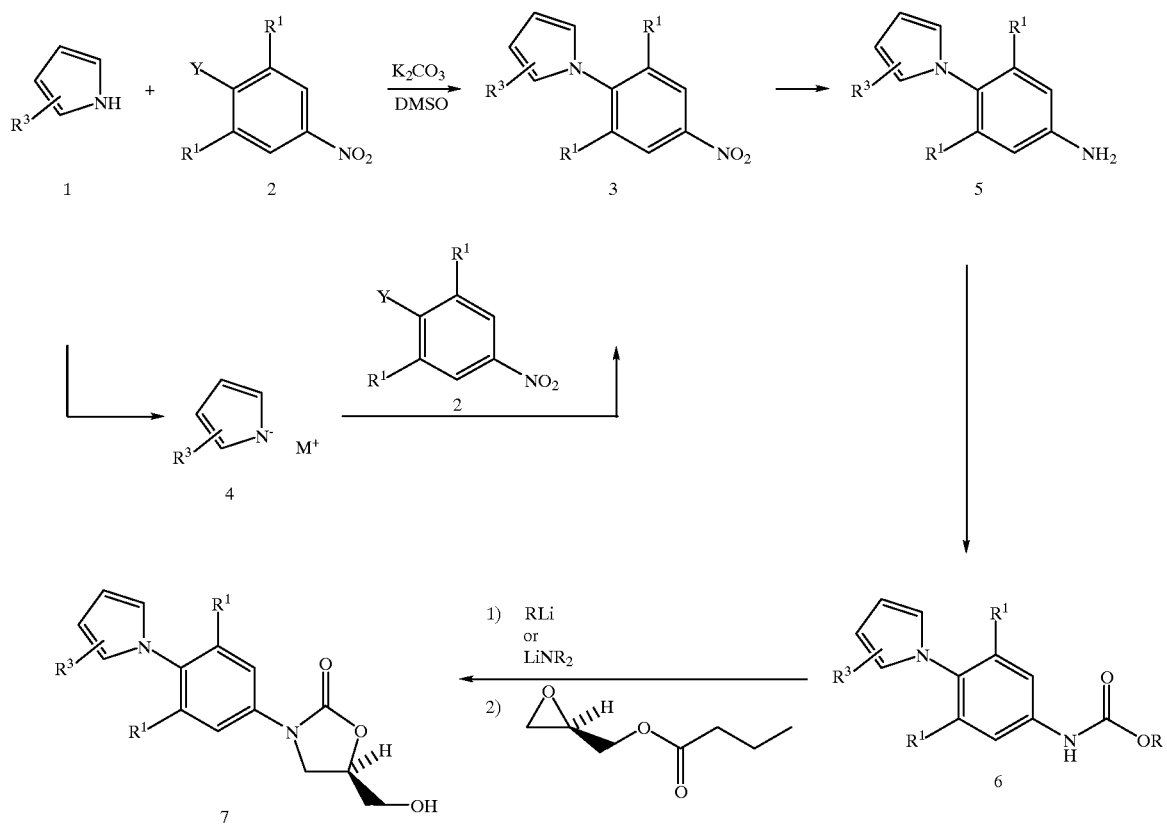
CHART II
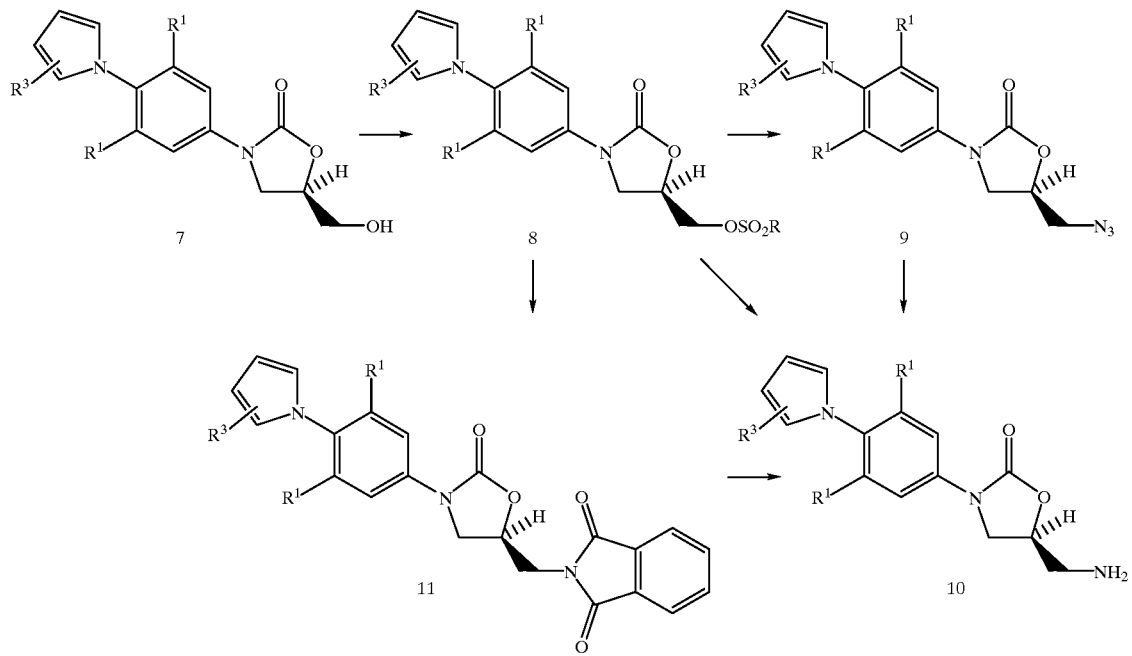

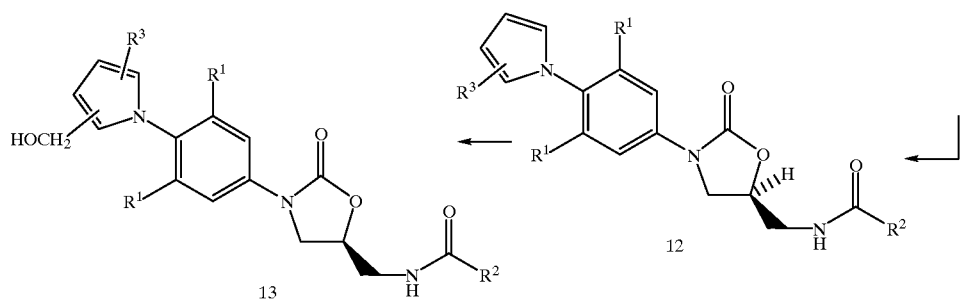
CHART III
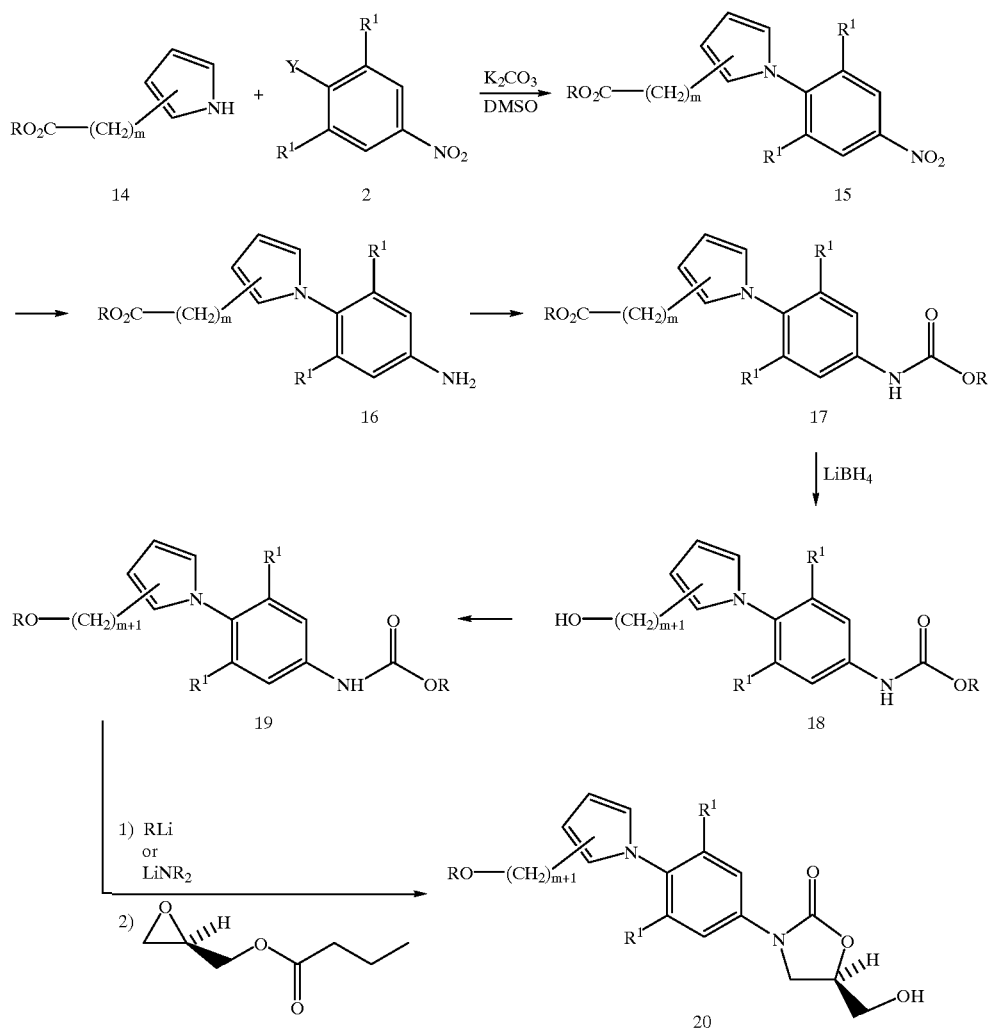
CHART IV
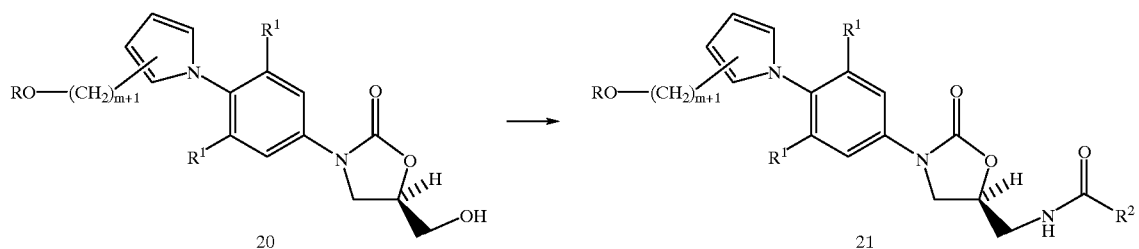

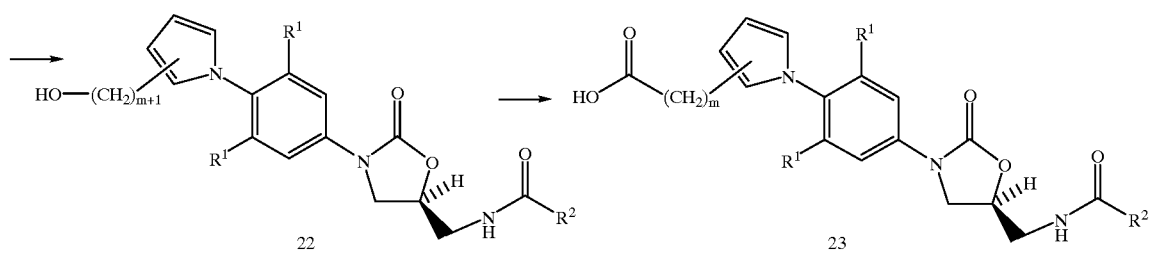
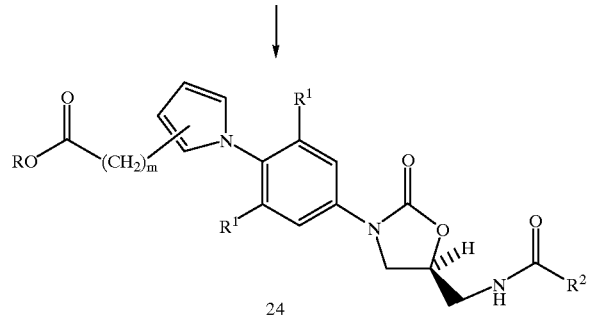
CHART V
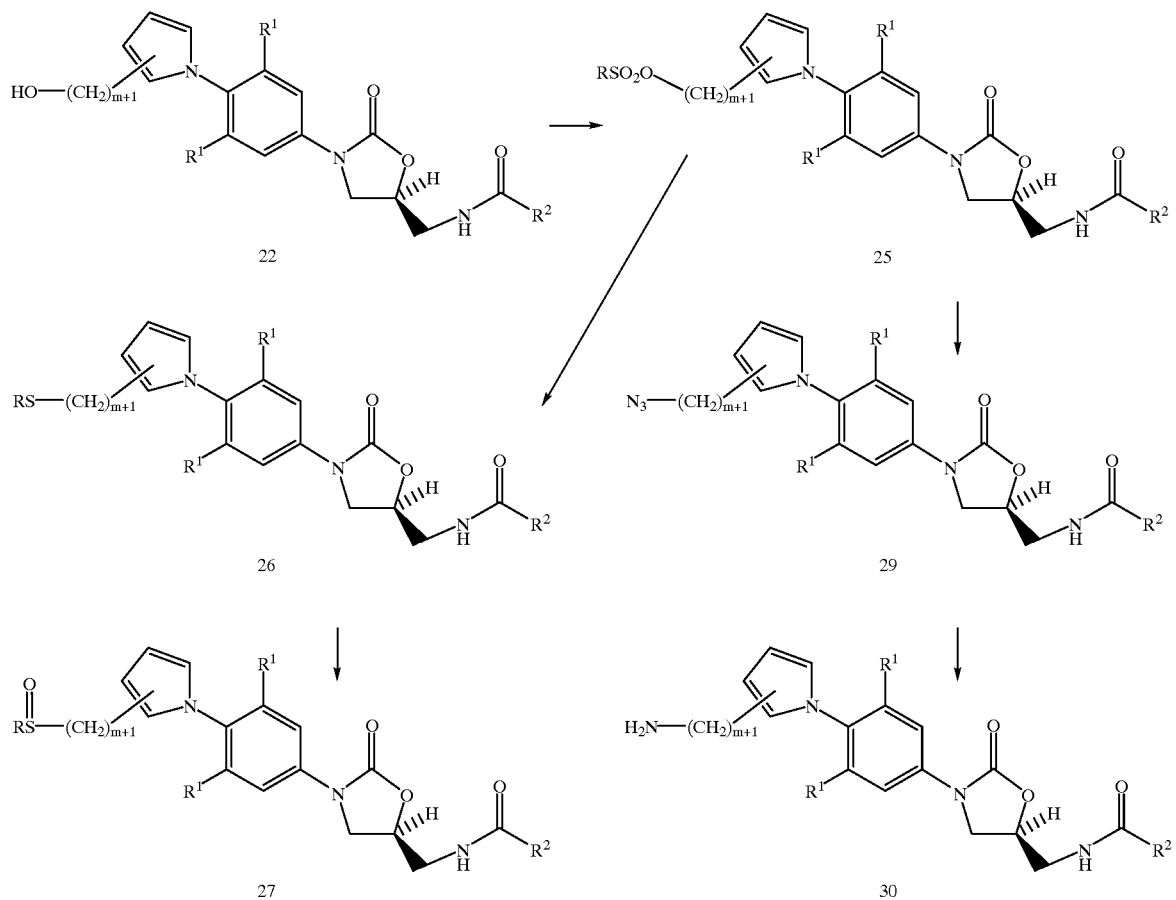

39 40
-continued
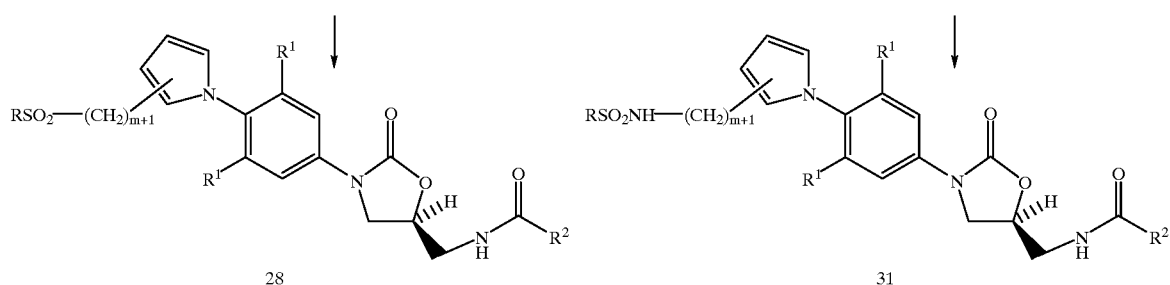
28 31
CHART VI
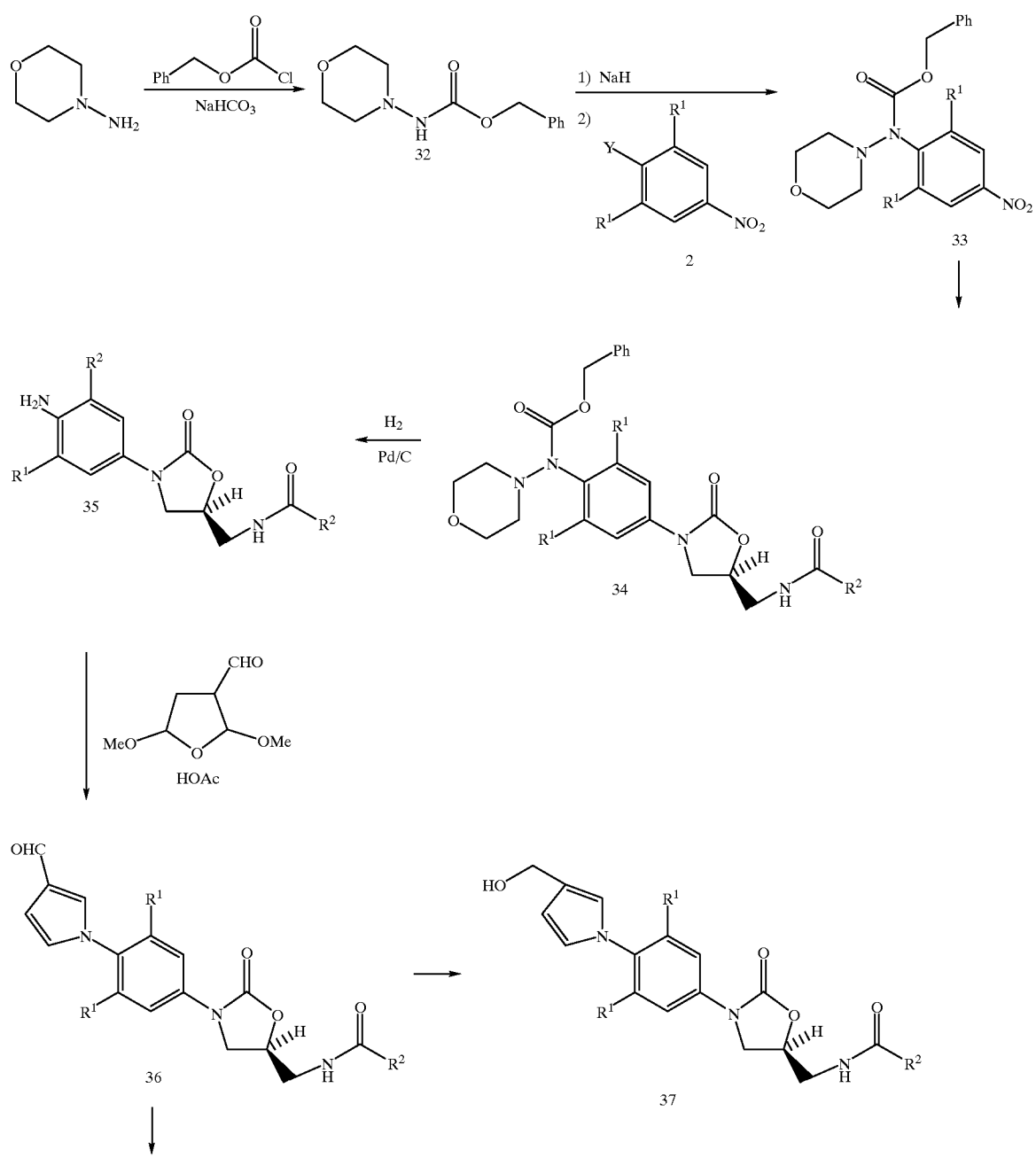

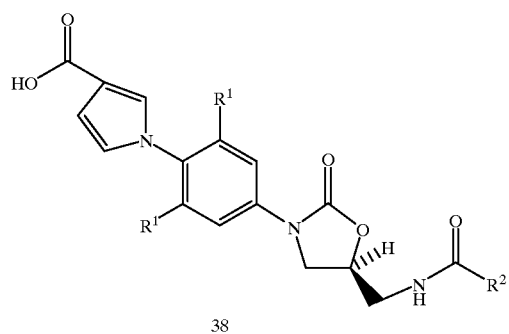
38
CHART VII
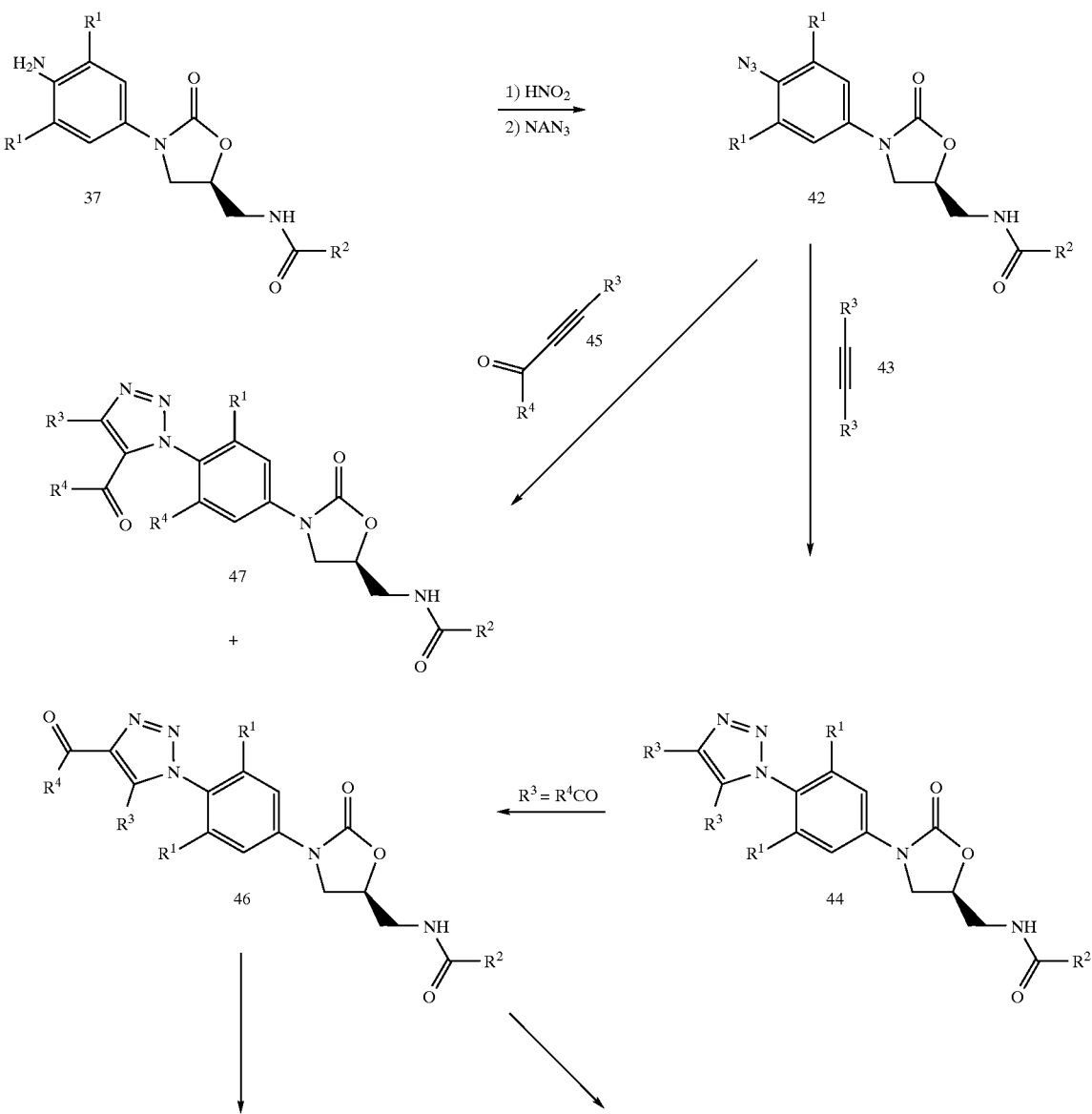

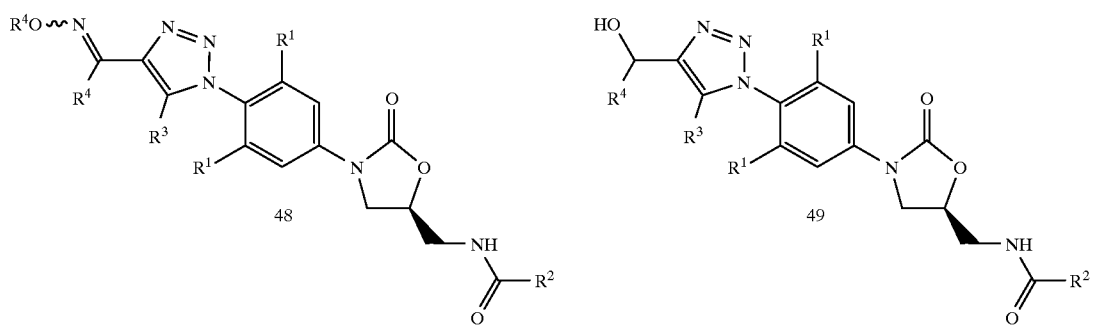
CHART VIII
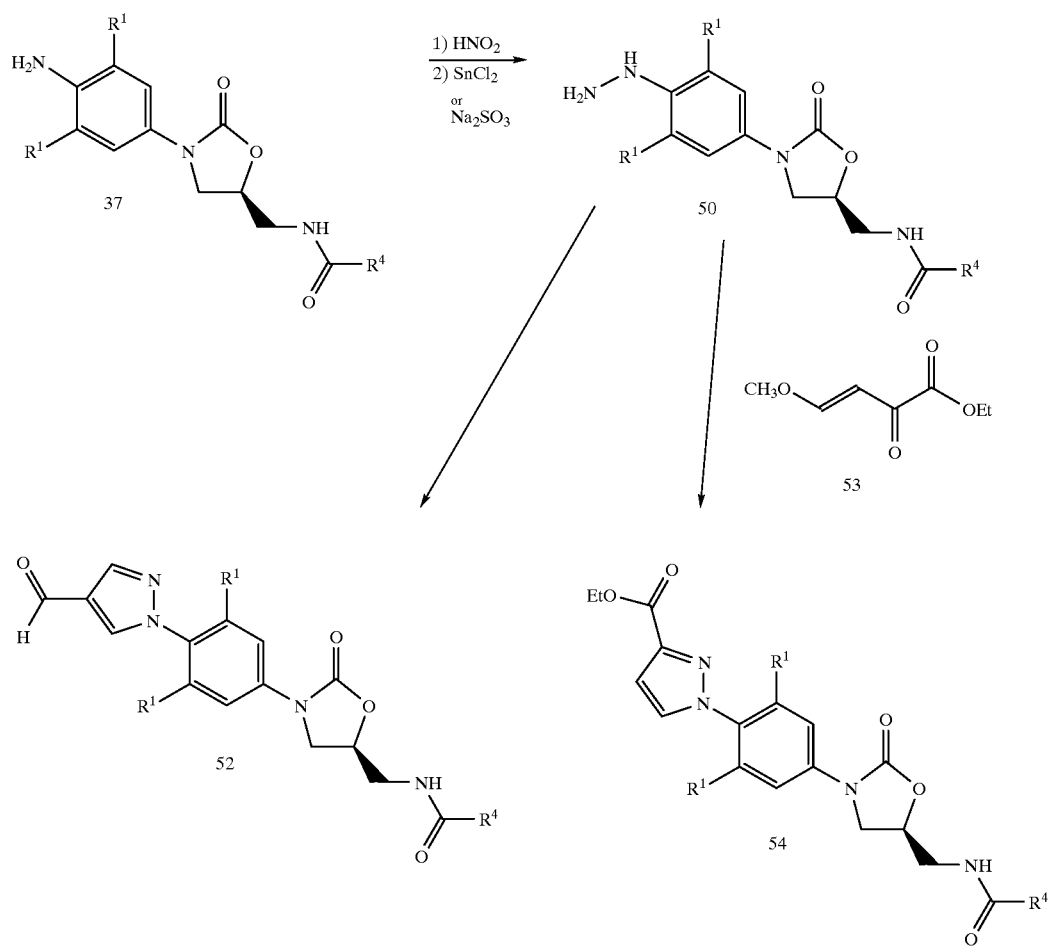

What is claimed is:

1. A compound structurally represented by Formula I

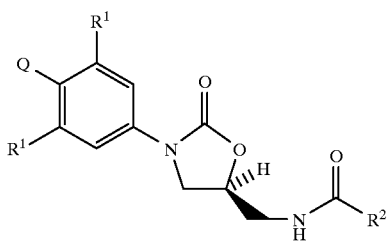

I or pharmaceutically acceptable salts thereof wherein:

Q is a hetero-aromatic 5-member ring bound to the aromatic ring of I at the nitrogen of the structures i, ii, iii, iv, v, vi, vii, viii, or ix:

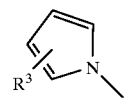

i

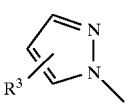

ii

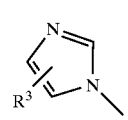

iii

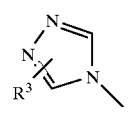

iv

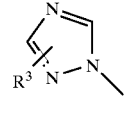

v

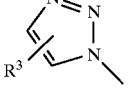

vi

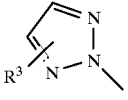

vii

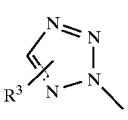

viii

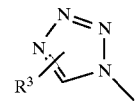

ix or alternatively Q can be a benzoannulated hetero-aromatic 5-member ring bound to the aromatic ring of I at the nitrogen of the structures x, xi, xii, or xiii;

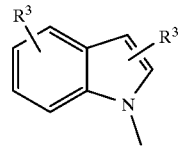

x

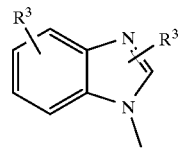

xi

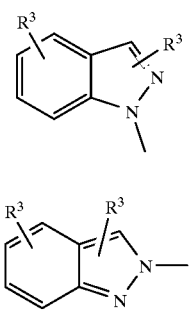

xii xiii $R^1$ is independently
 (a) H,
 (b) —$OCH_3$,
 (c) F, or
 (d) Cl;

$R^2$ is
 (a) hydrogen,
 (b) $C_1$–$C_8$ alkyl, optionally substituted with one or more F, Cl, hydroxy, $C_1$–$C_8$ alkoxy, or $C_1$–$C_8$ acyloxy,
 (c) $C_3$–$C_6$ cycloalkyl,
 (d) amino,
 (e) $C_1$–$C_8$ alkylamino,
 (f) $C_1$–$C_8$ dialkylamino, or
 (g) $C_1$–$C_8$ alkoxy;

$R^3$ is each independently selected from
 (a) H,
 (b) F, Cl, Br,
 (c) —$OR^4$,
 (d) —$SR^4$,
 (e) —$S(O)_nR^4$ (n is 1 or 2),
 (f) —CN,
 (g) —$O_2CR^4$,
 (h) —$NHCOR^4$,
 (i) —$NHCO_2R^4$,
 (j) —$NHSO_2R^4$,
 (k) —$CO_2R^4$,
 (l) —$CON(R^4)_2$, (m) —COR⁴,
(n) $C_1$–$C_8$ straight or branched chain alkyl or $C_3$–$C_8$ cycloalkyl, optionally substituted with one or more of (a)–(m),
(o) Phenyl, optionally substituted with one or more of the preceding groups listed under (a)–(n),
(p) —CH=CHCO₂Et, or
(q) —C(=NR₅)R₆, wherein R₅ is —OH or OCH₃, wherein R₆ is H or CH₃; and R⁴ is
 (a) H,
 (b) $C_1$–$C_6$ straight or branched chain alkyl or $C_3$–$C_8$ cycloalkyl, optionally substituted with one or more fluorine, chlorine, hydroxy, $C_1$–$C_4$ alkoxy, $C_1$–$C_4$ acyl, $C_1$–$C_4$ acyloxy, or O₂CCH₂N(CH₃)₂, or
 (c) Phenyl, optionally substituted with one or more of fluorine, chlorine, $C_1$–$C_4$ straight or branched chain alkyl, hydroxy, $C_1$–$C_4$ alkoxy, $C_1$–$C_4$ acyl, $C_1$–$C_4$ acyloxy, or O₂CCH₂N(CH₃)₂.

2. The compound of claim 1 wherein Q is i.
3. The compound of claim 1 wherein Q is ii.
4. The compound of claim 1 wherein Q is iii.
5. The compound of claim 1 wherein Q is iv.
6. The compound of claim 1 wherein Q is v.
7. The compound of claim 1 wherein Q is vi.
8. The compound of claim 1 wherein Q is vii.
9. The compound of claim 1 wherein Q is viii.
10. The compound of claim 1 wherein Q is ix.
11. The compound of claim 1 wherein R¹ is F.
12. The compound of claim 1 wherein R¹ is H.
13. The compound of claim 1 wherein R² is methyl, dichloromethyl, methoxy, or hydrogen.
14. The compound of claim 1 wherein R³ is hydrogen, $C_1$–$C_8$ alkylhydroxy, $C_1$–$C_8$ alkyl or $C_1$–$C_4$ alkoxycarbonyl.
15. A compound of claim 1 which is
 (a) (S)-N-[[3-[3-Fluoro-4-(1H-pyrrol-1-yl)phenyl]-2-oxo-5-oxazolidinyl]methyl]acetamide;
 (b) (S)-N-[[3-[3-Fluoro-4-(3-carbomethoxy-1H-pyrrol-1-yl)phenyl]-2-oxo-5-oxazolidinyl]methyl]acetamide;
 (c) (S)-N-[[3-[3-Fluoro-4-(1H-pyrrol-1-yl-3-carboxaldehyde)phenyl]-2-oxo-5-oxazolidinyl]methyl]acetamide;
 (d) (S)-N-[[3-[3-Fluoro-4-(3-(hydroxyiminomethyl)-1H-pyrrol-1-yl)phenyl]-2-oxo-5-oxazolidinyl]methyl]acetamide;
 (e) (S)-N-[[3-[3-Fluoro-4-(3-(methoxyiminomethyl)-1H-pyrrol-1-yl)phenyl]-2-oxo-5-oxazolidinyl]methyl]acetamide;
 (f) (S)-N-[[3-[3-Fluoro-4-(3-hydroxymethyl-1H-pyrrol-1-yl)phenyl]-2-oxo-5-oxazolidinyl]methyl]acetamide;
 (g) (S)-N-[[3-[3-Fluoro-4-[3-(2-carboethoxyvinyl)-1H-pyrrol-1-yl]phenyl]-2-oxo-5-oxazolidinyl]methyl]acetamide;
 (h) (S)-N-[[3-[3-Fluoro-4-[3-(2-carboethoxyethyl)-1H-pyrrol-1-yl]phenyl]-2-oxo-5-oxazolidinyl]methyl]acetamide;
 (i) (S)-N-[[3-[3-Fluoro-4-[3-(3-hydroxypropyl)-1H-pyrrol-1-yl]phenyl]-2-oxo-5-oxazolidinyl]methyl]acetamide;
 (j) (S)-N-[[3-[3-Fluoro-4-[3-(3-methanesulfonylaminopropyl)-1H-pyrrol-1-yl]phenyl]-2-oxo-5-oxazolidinyl]methyl]acetamide;
 (k) (S)-N-[[3-[3-Fluoro-4-(1H-imidazol-1-yl)phenyl]-2-oxo-5-oxazolidinyl]methyl]acetamide;
 (l) (S)-N-[[3-[3-Fluoro-4-(4-methyl-1H-imidazol-1-yl)phenyl]-2-oxo-5-oxazolidinyl]methyl]acetamide;
 (m) (S)-N-[[3-[3-Fluoro-4-(4-ethyl-1H-imidazol-1-yl)phenyl]-2-oxo-5-oxazolidinyl]methyl]acetamide;
 (n) (S)-N-[[3-[3-Fluoro-4-[4-(carbomethoxy)-1H-imidazol-1-yl]phenyl]-2-oxo-5-oxazolidinyl]methyl]acetamide;
 (o) (S)-N-[[3-[3-Fluoro-4-[4-(hydroxymethyl)-1H-imidazol-1-yl]phenyl]-2-oxo-5-oxazolidinyl]methyl]acetamide;
 (p) (S)-N-[[3-[3-Fluoro-4-[4-(2-hydroxyethyl)-1H-imidazol-1-yl]phenyl]-2-oxo-5-oxazolidinyl]methyl]acetamide;
 (q) (S)-N-[[3-[3-Fluoro-4-[1H-imidazol-1-yl-4-carboxaldehyde]phenyl]-2-oxo-5-oxazolidinyl]methyl]acetamide;
 (r) (S)-N-[[3-[3-Fluoro-4-[3-(hydroxyiminomethyl)-1H-imidazol-1-yl]phenyl]-2-oxo-5-oxazolidinyl]methyl]acetamide;
 (s) (S)-N-[[3-[3-Fluoro-4-[3-(methoxyiminomethyl)-1H-imidazol-1-yl]phenyl]-2-oxo-5-oxazolidinyl]methyl]acetamide;
 (t) (S)-N-[[3-[3-Fluoro-4-(1H-pyrazol-1-yl)phenyl]-2-oxo-5-oxazolidinyl]methyl]acetamide;
 (u) (S)-N-[[3-[3-Fluoro-4-(4-methyl-1H-pyrazol-1-yl)phenyl]-2-oxo-5-oxazolidinyl]methyl]acetamide;
 (v) (S)-N-[[3-[3-Fluoro-4-[3-(hydroxymethyl)-1H-pyrazol-1-yl]phenyl]-2-oxo-5-oxazolidinyl]methyl]acetamide;
 (w) (S)-N-[[3-[3-Fluoro-4-[3-(carbomethoxy)-1H-pyrazol-1-yl]phenyl]-2-oxo-5-oxazolidinyl]methyl]acetamide;
 (x) (S)-N-[[3-[3-Fluoro-4-(1H-pyrazol-1-yl-3-carboxaldehyde)phenyl]-2-oxo-5-oxazolidinyl]methyl]acetamide;
 (y) (S)-N-[[3-[3-Fluoro-4-(3-(hydroxyiminomethyl)-1H-pyrazol-1-yl]phenyl]-2-oxo-5-oxazolidinyl]methyl]acetamide;
 (z) (S)-N-[[3-[3-Fluoro-4-(3-(methoxyiminomethyl)-1H-pyrazol-1-yl]phenyl]-2-oxo-5-oxazolidinyl]methyl]acetamide;
 (aa) (S)-N-[[3-[3-Fluoro-4-[4-(hydroxymethyl)-1H-pyrazol-1-yl]phenyl]-2-oxo-5-oxazolidinyl]methyl]acetamide;
 (bb) (S)-N-[[3-[3-Fluoro-4-[4-(carbomethoxy)-1H-pyrazol-1-yl]phenyl]-2-oxo-5-oxazolidinyl]methyl]acetamide;
 (cc) (S)-N-[[3-[3-Fluoro-4-(1H-pyrazol-1-yl-4-carboxaldehyde)phenyl]-2-oxo-5-oxazolidinyl]methyl]acetamide;
 (dd) (S)-N-[[3-[3-Fluoro-4-(4-(hydroxyiminomethyl)-1H-pyrazol-1-yl)phenyl]-2-oxo-5-oxazolidinyl]methyl]acetamide;
 (ee) (S)-N-[[3-[3-Fluoro-4-(4-(methoxyiminomethyl)-1H-pyrazol-1-yl)phenyl]-2-oxo-5-oxazolidinyl]methyl]acetamide;
 (ff) (S)-N-[[3-[3-Fluoro-4-(1H-1,2,4-triazol-1-yl)phenyl]-2-oxo-5-oxazolidinyl]methyl]acetamide;
 (gg) (S)-N-[3-[3-Fluoro-4-[3-mercapto-4H-1,2,4-triazol-4-yl]phenyl]-2-oxo-5-oxazolidinyl]methylacetamide;
 (hh) (S)-N-[3-[3-Fluoro-4-[3-methylthio-4H-1,2,4-triazol-4-yl]phenyl]-2-oxo-5-oxazolidinyl]methylacetamide;
 (ii) (S)-N-[3-[3-Fluoro-4-[4H-1,2,4-triazol-4-yl]phenyl]-2-oxo-5-oxazolidinyl]methylacetamide;

(jj) (S)-N-[[3-[3-Fluoro-4-(1H-1,2,3-triazol-1-yl)phenyl]-2-oxo-5-oxazolidinyl]methyl]acetamide;
(kk) (S)-N-[[3-[3-Fluoro-4-(4-carbomethoxy-1H-1,2,3-triazol-1-yl)phenyl]-2-oxo-5-oxazolidinyl]methyl]acetamide;
(ll) (S)-N-[[3-[3-Fluoro-4-(4-(hydroxymethyl)-1H-1,2,3-triazol-1-yl)phenyl]-2-oxo-5-oxazolidinyl]methyl]acetamide;
(mm) (S)-N-[[3-[3-Fluoro-4-(4-(1-hydroxyethyl)-1H-1,2,3-triazol-1-yl)phenyl]-2-oxo-5-oxazolidinyl]methyl]acetamide;
(nn) (S)-N-[[3-[3-Fluoro-4-(1H-1,2,3-triazol-1-yl-4-carboxaldehyde)phenyl]-2-oxo-5-oxazolidinyl]methyl]acetamide;
(oo) (S)-N-[[3-[3-Fluoro-4-(4-(hydroxyiminomethyl)-1H-1,2,3-triazol-1-yl)phenyl]-2-oxo-5-oxazolidinyl]methyl]acetamide, oxime;
(pp) (S)-N-[[3-[3-Fluoro-4-(4-(methoxyiminomethyl)-1H-1,2,3-triazol-1-yl)phenyl]-2-oxo-5-oxazolidinyl]methyl]acetamide;
(qq) (S)-N-[[3-[3-Fluoro-4-(4-acetyl-1H-1,2,3-triazol-1-yl)phenyl]-2-oxo-5-oxazolidinyl]methyl]acetamide;
(rr) (S)-N-[[3-[3-Fluoro-4-(4-(1-hydroxyiminoethyl)-1H-1,2,3-triazol-1-yl)phenyl]-2-oxo-5-oxazolidinyl]methyl]acetamide;
(ss) (S)-N-[[3-[3-Fluoro-4-(4-(1-methoxyiminoethyl)-1H-1,2,3-triazol-1-yl)phenyl]-2-oxo-5-oxazolidinyl]methyl]acetamide;
(tt) (S)-N-[[3-[3-Fluoro-4-(2H-1,2,3-triazol-2-yl)phenyl]-2-oxo-5-oxazolidinyl]methyl]acetamide;
(uu) (S)-N-[[3-[3-Fluoro-4-(1H-1,2,3,4-tetrazol-1-yl)phenyl]-2-oxo-5-oxazolidinyl]methyl]acetamide;
(vv) (S)-N-[[3-[3-Fluoro-4-(2H-1,2,3,4-tetrazol-2-yl)phenyl]-2-oxo-5-oxazolidinyl]methyl]acetamide;
(ww) (S)-N-[[3-[3-Fluoro-4-(1H-indol-1-yl)phenyl]-2-oxo-5-oxazolidinyl]methyl]acetamide;
(xx) (S)-N-[[3-[3-Fluoro-4-(7-aza-1H-indol-1-yl)phenyl]-2-oxo-5-oxazolidinyl]methyl]acetamide;
(yy) (S)-N-[[3-[3-Fluoro-4-(1H-benzimidazol-1-yl)phenyl]-2-oxo-5-oxazolidinyl]methyl]acetamide;
(zz) (S)-N-[[3-[3-Fluoro-4-(1H-indazol-1-yl)phenyl]-2-oxo-5-oxazolidinyl]methyl]acetamide;
(aaa) (S)-N-[[3-[3-Fluoro-4-(1H-benzotriazol-1-yl)phenyl]-2-oxo-5-oxazolidinyl]methyl]acetamide;
(bbb) (S)-N-[[3-[3-Fluoro-4-(1H-1,2,3-triazol-1-yl)phenyl]-2-oxo-5-oxazolidinyl]methyl]-2,2-dichloroacetamide; or
(ccc) (S)-N-[[3-[3-Fluoro-4-(1H-1,2,3-triazolo[4,5b]-pyridin-1-yl)phenyl]-2-oxo-5-oxazolidinyl]methyl]acetamide.

16. A compound of 1 which is
(a) (S)-N-[[3-[3-Fluoro-4-(1H-pyrrol-1-yl)phenyl]-2-oxo-5-oxazolidinyl]methyl]acetamide;
(b) (S)-N-[[3-[3-Fluoro-4-(3-carbomethoxy-1H-pyrrol-1-yl)phenyl]-2-oxo-5-oxazolidinyl]methyl]acetamide;
(c) (S)-N-[[3-[3-Fluoro-4-(1H-pyrrol-1-yl-3-carboxaldehyde)phenyl]-2-oxo-5-oxazolidinyl]methyl]acetamide;
(d) (S)-N-[[3-[3-Fluoro-4-(3-(hydroxyiminomethyl)-1H-pyrrol-1-yl)phenyl]-2-oxo-5-oxazolidinyl]methyl]acetamide;
(e) (S)-N-[[3-[3-Fluoro-4-(3-(methoxyiminomethyl)-1H-pyrrol-1-yl)phenyl]-2-oxo-5-oxazolidinyl]methyl]acetamide;
(f) (S)-N-[[3-[3-Fluoro-4-(3-hydroxymethyl-1H-pyrrol-1-yl)phenyl]-2-oxo-5-oxazolidinyl]methyl]acetamide;
(g) (S)-N-[[3-[3-Fluoro-4-[3-(2-carboethoxyvinyl)-1H-pyrrol-1-yl)phenyl]-2-oxo-5-oxazolidinyl]methyl]acetamide;
(h) (S)-N-[[3-[3-Fluoro-4-[3-(2-carboethoxyethyl)-1H-pyrrol-1-yl)phenyl]-2-oxo-5-oxazolidinyl]methyl]acetamide;
(i) (S)-N-[[3-[3-Fluoro-4-[3-(3-hydroxypropyl)-1H-pyrrol-1-yl)phenyl]-2-oxo-5-oxazolidinyl]methyl]acetamide;
(j) (S)-N-[[3-[3-Fluoro-4-[3-(3-methanesulfonylaminopropyl)-1H-pyrrol-1-yl]phenyl]-2-oxo-5-oxazolidinyl]methyl]acetamide;
(k) (S)-N-[[3-[3-Fluoro-4-(1H-imidazol-1-yl)phenyl]-2-oxo-5-oxazolidinyl]methyl]acetamide;
(l) (S)-N-[[3-[3-Fluoro-4-(1H-pyrazol-1-yl)phenyl]-2-oxo-5-oxazolidinyl]methyl]acetamide;
(m) (S)-N-[[3-[3-Fluoro-4-[4-(hydroxymethyl)-1H-pyrazol-1-yl)phenyl]-2-oxo-5-oxazolidinyl]methyl]acetamide;
(n) (S)-N-[[3-[3-Fluoro-4-(1H-1,2,4-triazol-1-yl)phenyl]-2-oxo-5-oxazolidinyl]methyl]acetamide;
(o) (S)-N-[3-[3-Fluoro-4-[3-mercapto-4H-1,2,4-triazol-4-yl]phenyl]-2-oxo-5-oxazolidinyl]methylacetamide;
(p) (S)-N-[3-[3-Fluoro-4-[3-methylthio-4H-1,2,4-triazol-4-yl]phenyl]-2-oxo-5-oxazolidinyl]methylacetamide;
(q) (S)-N-[3-[3-Fluoro-4-[4H-1,2,4-triazol-4-yl]phenyl]-2-oxo-5-oxazolidinyl]methylacetamide;
(r) (S)-N-[[3-[3-Fluoro-4-(1H-1,2,3-triazol-1-yl)phenyl]-2-oxo-5-oxazolidinyl]methyl]acetamide;
(s) (S)-N-[[3-[3-Fluoro-4-(4-carbomethoxy-1H-1,2,3-triazol-1-yl)phenyl]-2-oxo-5-oxazolidinyl]methyl]acetamide;
(t) (S)-N-[[3-[3-Fluoro-4-(4-(1-hydroxyethyl)-1H-1,2,3-triazol-1-yl)phenyl]-2-oxo-5-oxazolidinyl]methyl]acetamide;
(u) (S)-N-[[3-[3-Fluoro-4-(1H-1,2,3-triazol-1-yl-4-carboxaldehyde)phenyl]-2-oxo-5-oxazolidinyl]methyl]acetamide;
(v) (S)-N-[[3-[3-Fluoro-4-(4-(hydroxyiminomethyl)-1H-1,2,3-triazol-1-yl)phenyl]-2-oxo-5-oxazolidinyl]methyl]acetamide;
(w) (S)-N-[[3-[3-Fluoro-4-(4-acetyl-1H-1,2,3-triazol-1-yl)phenyl]-2-oxo-5-oxazolidinyl]methyl]acetamide;
(x) (S)-N-[[3-[3-Fluoro-4-(2H-1,2,3-triazol-2-yl)phenyl]-2-oxo-5-oxazolidinyl]methyl]acetamide;
(y) (S)-N-[[3-[3-Fluoro-4-(1H-indol-1-yl)phenyl]-2-oxo-5-oxazolidinyl]methyl]acetamide; or
(z) (S)-N-[[3-[3-Fluoro-4-(1H-1,2,3-triazol-1-yl)phenyl]-2-oxo-5-oxazolidinyl]methyl]-2,2-dichloroacetamide.

17. A compound of 1 which is
(a) (S)-N-[[3-[3-Fluoro-4-(1H-pyrrol-1-yl)phenyl]-2-oxo-5-oxazolidinyl]methyl]acetamide;
(b) (S)-N-[[3-[3-Fluoro-4-(3-carbomethoxy-1H-pyrrol-1-yl)phenyl]-2-oxo-5-oxazolidinyl]methyl]acetamide;
(c) (S)-N-[[3-[3-Fluoro-4-(3-(hydroxyiminomethyl)-1H-pyrrol-1-yl)phenyl]-2-oxo-5-oxazolidinyl]methyl]acetamide;
(d) (S)-N-[[3-[3-Fluoro-4-(3-(methoxyiminomethyl)-1H-pyrrol-1-yl)phenyl]-2-oxo-5-oxazolidinyl]methyl]acetamide;
(e) (S)-N-[[3-[3-Fluoro-4-[3-(2-carboethoxyethyl)-1H-pyrrol-1-yl)phenyl]-2-oxo-5-oxazolidinyl]methyl]acetamide;

(f) (S)-N-[[3-[3-Fluoro-4-(1H-imidazol-1-yl)phenyl]-2-oxo-5-oxazolidinyl]methyl]acetamide;

(g) (S)-N-[[3-[3-Fluoro-4-(1H-pyrazol-1-yl)phenyl]-2-oxo-5-oxazolidinyl]methyl]acetamide;

(h) (S)-N-[[3-[3-Fluoro-4-(1H-1,2,4-triazol-1-yl)phenyl]-2-oxo-5-oxazolidinyl]methyl]acetamide;

(i) (S)-N-[[3-[3-Fluoro-4-(1H-1,2,3-triazol-1-yl)phenyl]-2-oxo-5-oxazolidinyl]methyl]acetamide;

(j) (S)-N-[[3-[3-Fluoro-4-(4-carbomethoxy-1H-1,2,3-triazol-1-yl)phenyl]-2-oxo-5-oxazolidinyl]methyl]acetamide;

(k) (S)-N-[[3-[3-Fluoro-4-(4-acetyl-1H-1,2,3-triazol-1-yl)phenyl]-2-oxo-5-oxazolidinyl]methyl]acetamide; or (l) (S)-N-[[3-[3-Fluoro-4-(2H-1,2,3-triazol-2-yl)phenyl]-2-oxo-5-oxazolidinyl]methyl]acetamide.

18. A method for treating microbial infections in patients suffering therefrom comprising administering an antibacterially effective amount of a compound of Formula I.

19. The method of claim 9 wherein the antibacterially effective amount is from about 0.1 to about 100 mg/kg of body weight/day.

* * * * *